US008841110B2

(12) United States Patent
Xiang et al.

(10) Patent No.: US 8,841,110 B2
(45) Date of Patent: *Sep. 23, 2014

(54) ANIMAL PRODUCT FREE SYSTEM AND PROCESS FOR PURIFYING A BOTULINUM TOXIN

(71) Applicant: Allergan, Inc., Irvine, CA (US)

(72) Inventors: Hui Xiang, Irvine, CA (US); Mingjiang Luo, Tustin, CA (US); Ping Wang, Irvine, CA (US); Stephen Donovan, Capistano Beach, CA (US)

(73) Assignee: Allergan, Inc., Irvine, CA (US)

( * ) Notice: Subject to any disclaimer, the term of this patent is extended or adjusted under 35 U.S.C. 154(b) by 36 days.

This patent is subject to a terminal disclaimer.

(21) Appl. No.: 13/781,126

(22) Filed: Feb. 28, 2013

(65) Prior Publication Data

US 2013/0171716 A1    Jul. 4, 2013

Related U.S. Application Data

(63) Continuation of application No. 12/098,896, filed on Apr. 7, 2008, now Pat. No. 8,409,828, which is a continuation of application No. 11/072,673, filed on Mar. 3, 2005, now Pat. No. 7,354,740, which is a continuation-in-part of application No. 11/072,050, filed on Mar. 3, 2005, now Pat. No. 7,160,699, which is a continuation-in-part of application No. 10/672,876, filed on Sep. 25, 2003, now Pat. No. 7,148,041.

(51) Int. Cl.
*C12N 9/52* (2006.01)
*A61K 39/08* (2006.01)

(52) U.S. Cl.
USPC ..... 435/220; 435/71.1; 424/239.1; 424/236.1

(58) Field of Classification Search
USPC ........... 435/71.1, 252.7, 253.6, 220; 424/842, 424/236.1, 239.1
See application file for complete search history.

(56) References Cited

U.S. PATENT DOCUMENTS

| | | | |
|---|---|---|---|
| 4,401,683 A | 8/1983 | Thompson | |
| 5,437,291 A | 8/1995 | Pasricha | 127/898 |
| 5,670,484 A | 9/1997 | Binder | 514/14 |
| 5,714,468 A | 2/1998 | Binder | 514/14 |
| 5,766,605 A | 6/1998 | Sanders | 424/239.1 |
| 5,861,431 A | 1/1999 | Hildebrand et al. | 514/557 |
| 6,063,768 A | 5/2000 | First | 514/14 |
| 6,139,845 A | 10/2000 | Donovan | 424/236.1 |
| 6,265,379 B1 | 7/2001 | Donovan | 514/14 |
| 6,296,847 B1 | 10/2001 | Gokcen et al. | 424/94.2 |
| 6,299,893 B1 | 10/2001 | Schwartz | 424/422 |
| 6,306,423 B1 | 10/2001 | Donovan | 424/423 |
| 6,312,708 B1 | 11/2001 | Donovan | 424/423 |
| 6,358,926 B2 | 3/2002 | Donovan | 514/14 |
| 6,365,164 B1 | 4/2002 | Schmidt | 424/239.1 |
| 6,423,319 B1 | 7/2002 | Brooks | 424/239.1 |
| 6,458,365 B1 | 10/2002 | Aoki | 514/2 |
| 6,464,986 B1 | 10/2002 | Aoki | 514/2 |
| 6,558,926 B1 | 5/2003 | Demain et al. | |
| 6,818,409 B2 | 11/2004 | Oguma | |
| 7,148,041 B2 | 12/2006 | Donovan | |
| 7,160,699 B2 | 1/2007 | Wang et al. | |
| 7,354,740 B2 | 4/2008 | Xiang et al. | |
| 7,449,192 B2 | 11/2008 | Schmidt | |
| 7,452,697 B2 | 11/2008 | Luo et al. | |
| 7,455,845 B2 | 11/2008 | Schmidt et al. | |
| 7,470,431 B2 | 12/2008 | Schmidt et al. | |
| 7,538,097 B2 | 5/2009 | Frost | |
| 7,544,499 B2 | 6/2009 | Frost | |
| 8,129,139 B2 | 3/2012 | Ton et al. | |
| 8,409,828 B2 * | 4/2013 | Xiang et al. | 435/71.1 |
| 2002/0025327 A1 | 2/2002 | Schmidt | 424/239.1 |
| 2003/0113349 A1 | 6/2003 | Coleman | |
| 2003/0118598 A1 | 6/2003 | Hunt et al. | |
| 2004/0067235 A1 | 4/2004 | Doshi | 435/6 |
| 2004/0235139 A1 | 11/2004 | Demain et al. | |
| 2005/0260186 A1 | 11/2005 | Bookbinder | |
| 2006/0104968 A1 | 5/2006 | Frost | |
| 2006/0247201 A1 | 11/2006 | Frost | |
| 2007/0148156 A1 | 6/2007 | Frost | |
| 2007/0275110 A1 | 11/2007 | Dott et al. | 424/780 |
| 2008/0199452 A1 | 8/2008 | Gaylis et al. | |

FOREIGN PATENT DOCUMENTS

| | | | |
|---|---|---|---|
| WO | WO 94/09115 | 1/1993 | |
| WO | WO 96/05222 | 6/1995 | |
| WO | WO 98/54296 | 5/1998 | |
| WO | WO99/03483 | 1/1999 | A61K 35/00 |
| WO | WO 01/05997 | 7/2000 | |
| WO | WO 0136655 | 10/2000 | |
| WO | WO 01/58472 | 2/2001 | |
| WO | WO01/34176 A | 5/2001 | |
| WO | WO2004/010934 A2 | 2/2004 | |
| WO | WO 2005/035749 | 8/2004 | |

(Continued)

OTHER PUBLICATIONS

U.S. Appl. No. 09/978,982, filed Oct. 15, 2001, Schmidt.
U.S. Appl. No. 10/194,805, filed Jul. 11, 2002, Donovan.
Baumgartner G. Hyaluronidase in the therapy of malignant diseases. Wien Klin Wochenschr Suppl. 1987: 174:1-22. Abstract.
Bigalke H., et al., *Botulinum A Neurotoxin Inhibits Non-Cholinergic Synaptic Transmission in Mouse Spinal Cord Neurons in Culture*, Brain Research 360 (1985), pp. 318-324.

(Continued)

*Primary Examiner* — Chih-Min Kam
(74) *Attorney, Agent, or Firm* — Brigitte C. Phan; Ted Chan; Debra Condino

(57) ABSTRACT

Chromatographic processes and systems for purifying a botulinum toxin from an APF fermentation medium.

6 Claims, 9 Drawing Sheets

(56) References Cited

FOREIGN PATENT DOCUMENTS

| WO | WO2005/053733 A1 | 6/2005 | ............ A61K 38/38 |
| WO | WO2006/005912 A2 | 1/2006 | |
| WO | WO2006/138127 A | 12/2006 | |
| WO | WO2007/044809 A | 4/2007 | |
| WO | WO2008/030638 A | 3/2008 | ............ A61K 39/08 |

OTHER PUBLICATIONS

Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 31 (1981) 6; pp. 244-251.

Binz T. et al., The Complete Sequence of Botulinum Neurotoxin Type A and Comparison with Other Clostridial Neurotoxins, J Biological Chemistry 265(16), (1990), pp. 9153-9158.

Bushara K., *Botulinum toxin and rhinorrhea*, Otolaryngol Head Neck Surg. 114(3) (1996), 507.

Botulinum toxin type A in the treatment of focal, axillary and palmar hyperhidrosis and other hyperhidrotic conditions. European J. Neurology 6 (Supp 4) 1999, pp. S111-S115.

Gonelle-Gispert et al. SNAP-25a and -25b insoforms are both expressed in insulin-secreting cells and can function in insulin secretion. Biochem J 1;339 (pt 1) 1999, pp. 159-165.

Drugdex Evaluations, Hyaluronidas, publ. Thomson Healthcare, 1974-2008.

Bedu-Addo, F., et al. "Use of Biophysical characterization in preformulation development of a heavy-chain fragment of botulinum serotype B: Evaluation of suitable purification process conditions." *Pharmaceutical Research* 21.8 (2004): 1353:1361.

Bonventre, P.F., et al. "Physiology of toxin production by clostridium botulinum types A and B." *College of Medicine* 7:372-374, (1959).

Byrne, M., et al. "Purification, potency, and efficacy of the botulinum type A binding domain from *Pichia pastoris* as a recombinant vaccine candidate." *Infection and Immunity* 66.10 (1998): 4817-4822.

Chen, F., et al. "Biophysical characterization of the stability of the 150-kilodalton botulinum toxin, the nontoxic component and the 900-kilodalton botulinum toxin complex species." *Infection and Immunity* 66.6 (Jun. 1998): 2420-2425.

Coligan, John E., et al., Eds. "Chp. 1:1-88, Strategies of protein purification and characterization." *Current Protocols in Protein Science, Front Matter* Aug. 2003.

Coligan, John E. et al., Eds,"Chp 21:1-282, Peptidases." *Protocols in Protein Science, Front Matter*, Aug. 2003.

Gessler, F., et al. "Production and purification of *Clostridium botulinum* type C and D neurotoxin." *FEMS Immunology and Medical Microbiology* 24 (1999): 361-367.

Gimenez, J., et al. "Simplified purification method for *Clostridium botulinum* type E toxin." *Applied and Environmental Microbiology* 53.12 (Dec. 1987): 2827-2830.

Heenan, C.N., et al. *Lehensm.-Wiss. U.-Technol.* 35 (2002): 171-176.

Holdeman, L., et al. "A study of the nutritional requirements and toxin production of *Clostridium botulinum* type F." *Canadian Journal of Microbiology*, 11(1965): 1009-1019.

Huhtanen, C.N. "Some observations on a perigo-type inhibition of *Clostridium botulinum* in a simplified medium." *Journal of Milk Food Technology* 38.12 (Dec. 1975): 761-763.

Johnson, E., et al. "*Clostridium botulinum* and its neurotoxins: a metabolic and cellular perspective." *Toxicon* 39 (2001): 1703-1722.

Johnson, S., et al. "Scale-up of the fermentation and purification of the recombinant heavy chain fragment C of botulinum neurotoxin serotype F, expressed in *Pichia pastoris*." *Protein Expression and Purification* 32 (2003): 1-9.

Karasawa, T., et al. "A defined growth medium for *Clostridium difficle.*" *Microbiology* 141 (1995): 371-375.

Kohl, A., et al. "Comparison of the effect of botulinum toxin A (BOTOX®) with the highly-purified neurotoxin (NT201) in the extensor digitorum brevis muscle test." *Movement Disorders* 15(Suppl 3) (2000): 165.

Kozaki, H., et al. "Immunological characterization of papain-induced fragments of *Clostridium botulinum* type A neurotoxin and interaction of the fragments with brain synaptosomes." *Infection and Immunity* 57.9 (1989): 2634-2639.

Lewis, K.H., et al. "Practical media and control measures for highly toxic cultures of *Clostridium botulinum* type A." *Production of Botulinum Toxin* 213-230, (1947).

Li, Y., et al. "Expression and characterization of the heavy chain of tetanus toxin: reconstitution of the fully-recombinant dichain protein in active form." *Journal of Biochemistry* (Tokyo) 125.6 (Jun. 1999): 1200-1208.

Lungdahl, L.G., et al. "Working with anaerobic bacteria." *Manual of Industrial Microbiology and Biotechnology* 1986, Chapter 8: 84-96.

Miwa, Norinaga, et al. *International Journal of Food Microbiology* 49 (1999): 103-106.

Mueller, J.H., et al. "Variable factors influencing the product of tetanus toxin." *Journal of Bacteriology* Mar. 1954, 67.3: 271-277.

Naumann, M., et al. "Botulinum toxin type A in the treatment of focal, axillary and palmar hyperhidrosis and other hyperhidrotic conditions." *European Journal of Neurology* 6(Suppl 4) (1999): S111-S115.

"Oxoid, Product CM0149, Product Description." 1-2, (2004).

Ozutsumi, K., et al. "Rapid, simplified method for production and purification of tetanus toxin." *Applied and Environmental Microbiology* 49.4 (Apr. 1985): 939-943.

Porfirio, Z., et al. "Specific peptides of casein pancreatic digestion enhance the production of tetanus toxin." *Journal of Applied Microbiology* 83 (1997): 678-684.

Prabakaran, S., et al. "Botulinum neurotoxin types B and E: Purification, limited proteolysis by endoproteinase Glu-C and Pepsin, and comparison of their indentified cleaved sites relative to the three-dimensional structure of type A neurotoxin." *Toxicon* 39 (2001): 1515-1531.

Ragona, Rosario Marchese, et al. "Management of Parotid Sialocele with botulinum toxin." *The Laryngoscope* 109 (Aug. 1999): 1344-1346.

Schantz, E.J. et al., J. Jankovic ed. "Preparation and characterization of botulinum toxin type A for human treatment." *Neurological Disease and Therapy. Therapy with Botulinum Toxin* 25 (1994): 41-49.

Schantz, E.J. et al. "Properties and use of botulinum toxin and other microbial neurotoxins in medicine." *Microbiological Reviews* Mar. 1992: 80-99.

Schantz, E.J., et al., Lewis, G.E. "Use of Chrystalline type A botulinum toxin in medical research." *Biomedical Aspects of Botulism*, Academic Press, Inc., George E. Lewis, Jr., Ed., 1981: 143-150.

Schiefer-Ullrich, H., et al. "Comparative studies on physiology and taxonomy of obligatory purinolytic clostridia." *Archives of Microbiology* 138 (1984): 345-353.

Siegel, L.S. "Fermentation kinetics of botulinum toxin production (types A, B and E)." Biomedical aspects of botulism, New York: Academic Press 1981: 121-128.

Siegel, L.S. "Toxin production by *Clostridium botulinum* type A under various fermentation conditions." *Applied and Environmental Microbiology* Oct. 1979: 606-611.

Tse, et al. *European Journal of Ciochemistry* 122 (1982): 493-500.

Weatherly, G., et al. "Initial purification of recombinant botulinum neurotoxin fragments for pharmaceutical production using hydrophobic charge induction chromatography." *Journal of Chromatography A* 952 (2002): 99-110.

Whitmer, M.E. et al. "Development of improved defined media for *Clostridium botulinum* serotypes A, B and E." *Applied and Environmental Microbiology* 54.3 (Mar. 1988): 753-759.

Young-Perkins, et al. *Journal of Food Science* 52 (1987): 1084-1088.

\* cited by examiner

SDS-PAGE of Butyl and SP column samples

US 8,841,110 B2

ANIMAL PRODUCT FREE SYSTEM AND PROCESS FOR PURIFYING A BOTULINUM TOXIN

CROSS REFERENCE

This application is a continuation of U.S. application Ser. No. 12/098,896, filed Apr. 7, 2008, now U.S. Pat. No. 8,409,828, which is a continuation of U.S. application Ser. No. 11/072,673, now U.S. Pat. No. 7,354,740, filed Mar. 3, 2005, which is a continuation in part of U.S. patent application Ser. No. 11/072,050, filed Mar. 3, 2005, now U.S. Pat. No. 7,160,699, which is a continuation in part of U.S. application Ser. No. 10/672,876, filed Sep. 25, 2003, now U.S. Pat. No. 7,148,041, the entire contents of which applications are incorporated herein by reference.

BACKGROUND

The present invention relates to systems and processes for purifying a *Clostridium* toxin. In particular, the present invention relates to a chromatographic process for purifying a botulinum neurotoxin. A pharmaceutical composition suitable for administration to a human or animal for a therapeutic, diagnostic, research or cosmetic purpose can comprise an active ingredient. The pharmaceutical composition can also include one or more excipients, buffers, carriers, stabilizers, preservatives and/or bulking agents. The active ingredient in a pharmaceutical composition can be a biologic such as a botulinum toxin. The botulinum toxin active ingredient used to make a botulinum toxin pharmaceutical composition can be obtained through a multi step culturing, fermentation and compounding process which makes use of one or more animal derived products (such as meat broth and casein ingredients in one or more of the culture and fermentation media used to obtain a bulk botulinum toxin, and a blood fraction or blood derivative excipient in the final compounded botulinum toxin pharmaceutical composition). Administration to a patient of a pharmaceutical composition wherein the active ingredient biologic is obtained through a process which makes use of animal derived products can subject the patient to a potential risk of receiving various pathogens or infectious agents. For example, prions may be present in a pharmaceutical composition. A prion is a proteinaceous infectious particle which is hypothesized to arise as an abnormal conformational isoform from the same nucleic acid sequence which makes the normal protein. It has been further hypothesized that infectivity resides in a "recruitment reaction" of the normal isoform protein to the prion protein isoform at a post translational level. Apparently, the normal endogenous cellular protein is induced to misfold into a pathogenic prion conformation.

Creutzfeldt-Jacob disease is a rare neurodegenerative disorder of human transmissible spongiform encephalopathy where the transmissible agent is apparently an abnormal isoform of a prion protein. An individual with Creutzfeldt-Jacob disease can deteriorate from apparent perfect health to akinetic mutism within six months. Thus, a potential risk may exist of acquiring a prion mediated disease, such as Creutzfeldt-Jacob disease, from the administration of a pharmaceutical composition which contains a biologic, such as a botulinum toxin, obtained, purified or compounded using animal derived products.

Botulinum Toxin

The genus *Clostridium* has more than one hundred and twenty seven species, grouped by morphology and function. The anaerobic, gram positive bacterium *Clostridium botulinum* produces a potent polypeptide neurotoxin, botulinum toxin, which causes a neuroparalytic illness in humans and animals known as botulism. *Clostridium botulinum* and its spores are commonly found in soil and the bacterium can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of botulinum toxin (purified neurotoxin complex) type A is a $LD_{50}$ in mice. On a molar basis, botulinum toxin type A is 1.8 billion times more lethal than diphtheria, 600 million times more lethal than sodium cyanide, 30 million times more lethal than cobrotoxin and 12 million times more lethal than cholera. Singh, *Critical Aspects of Bacterial Protein Toxins*, pages 63-84 (chapter 4) of *Natural Toxins II*, edited by B. R. Singh et al., Plenum Press, New York (1976) (where the stated $LD_{50}$ of botulinum toxin type A of 0.3 ng equals 1 U is corrected for the fact that about 0.05 ng of BOTOX® equals 1 unit). BOTOX® is the trademark of a botulinum toxin type A purified neurotoxin complex available commercially from Allergan, Inc., of Irvine, Calif. One unit (U) of botulinum toxin is defined as the $LD_{50}$ upon intraperitoneal injection into female Swiss Webster mice weighing about 18-20 grams each. In other words, one unit of botulinum toxin is the amount of botulinum toxin that kills 50% of a group of female Swiss Webster mice. Seven generally immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke.

For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. The botulinum toxins apparently bind with high affinity to cholinergic motor neurons, are translocated into the neuron and block the presynaptic release of acetylcholine.

Botulinum toxins have been used in clinical settings for the treatment of e.g. neuromuscular disorders characterized by hyperactive skeletal muscles. Botulinum toxin type A has been approved by the U.S. Food and Drug Administration for the treatment of essential blepharospasm, strabismus and hemifacial spasm in patients over the age of twelve, for the treatment of cervical dystonia and for the treatment of glabellar line (facial) wrinkles. The FDA has also approved a botulinum toxin type B for the treatment of cervical dystonia. Clinical effects of peripheral injection (i.e. intramuscular or subcutaneous) botulinum toxin type A are usually seen within one week of injection, and often within a few hours after injection. The typical duration of symptomatic relief (i.e. flaccid muscle paralysis) from a single intramuscular injection of botulinum toxin type A can be about three months to about six months.

Although all the botulinum toxins serotypes apparently inhibit release of the neurotransmitter acetylcholine at the neuromuscular junction, they do so by affecting different neurosecretory proteins and/or cleaving these proteins at different sites. Botulinum toxin A is a zinc endopeptidase which can specifically hydrolyze a peptide linkage of the intracellular, vesicle associated protein SNAP-25. Botulinum type E also cleaves the 25 kiloDalton (kD) synaptosomal associated protein (SNAP-25), but targets different amino acid sequences within this protein, as compared to botulinum toxin type A. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain (H chain) and a cell surface receptor; the receptor is thought to be different for each serotype of botulinum toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino end segment of the H chain, $H_N$, which triggers a conformational change of the toxin in response to a pH of about 5.5 or lower. Endosomes are known to possess a proton pump which decreases intra endosomal pH. The conformational shift exposes hydrophobic residues in the toxin, which permits the toxin to embed itself in the endosomal membrane. The toxin then translocates through the endosomal membrane into the cytosol.

The last step of the mechanism of botulinum toxin activity appears to involve reduction of the disulfide bond joining the H and L chain. The entire toxic activity of botulinum and botulinum toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Botulinum neurotoxin, botulinum toxin B, D, F, and G cause degradation of synaptobrevin (also called vesicle-associated membrane protein (VAMP)), a synaptosomal membrane protein. Most of the VAMP present at the cytosolic surface of the synaptic vesicle is removed as a result of any one of these cleavage events. Each toxin specifically cleaves a different bond.

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with one or more associated non-toxin proteins. Thus, the botulinum toxin type A complex can be produced by Clostridial bacterium as 900 kD, 500 kD and 300 kD forms (approximate molecular weights). Botulinum toxin types B and $C_1$ are apparently produced as only a 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemagglutinin protein and a non-toxin and non-toxic nonhemagglutinin protein. Thus, a botulinum toxin complex can comprise a botulinum toxin molecule (the neurotoxic component) and one or more non toxic, hemagluttinin proteins and/or non toxin, non hemagluttinin proteins (the later can be referred to as NTNH proteins) These two types of non-toxin proteins (which along with the botulinum toxin molecule can comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex. The toxin complexes can be dissociated into toxin protein and hemagglutinin proteins by treating the complex with red blood cells at pH 7.3. or by subjecting the complex to a separation process, such as column chromatography, in a suitable buffer at a pH of about 7-8. The botulinum toxin protein has a marked instability upon removal of the hemagglutinin protein.

All the botulinum toxin serotypes are made by native *Clostridium botulinum* bacteria as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D, and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

The success of botulinum toxin type A to treat a variety of clinical conditions has led to interest in other botulinum toxin serotypes. Thus, at least botulinum toxins types, A, B, E and F have been used clinically in humans. Additionally, pure (approx 150 kDa) botulinum toxin has been used to treat humans. See e.g. Kohl A., et al., *Comparison of the effect of botulinum toxin A (Botox®) with the highly-purified neurotoxin (NT 201) in the extensor digitorum brevis muscle test*, Mov Disord 2000; 15(Suppl 3):165. Hence, a botulinum toxin pharmaceutical composition can be prepared using a pure (approx 150 kDa) botulinum toxin, as opposed to use of a botulinum toxin complex.

The type A botulinum toxin is known to be soluble in dilute aqueous solutions at pH 4-6.8. At pH above about 7 the stabilizing nontoxic proteins dissociate from the neurotoxin, resulting in a gradual loss of toxicity, particularly as the pH and temperature rise. Schantz E. J., et al *Preparation and characterization of botulinum toxin type A for human treatment* (in particular pages 44-45), being chapter 3 of Jankovic, J., et al, *Therapy with Botulinum Toxin*, Marcel Dekker, Inc (1994).

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can be stabilized with a stabilizing agent such as albumin and gelatin.

It has been reported that a botulinum toxin has been used in various clinical settings, including as follows:

(1) about 75-125 units of BOTOX® per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (*European J. Neurology* 6 (Supp 4): S111-S1150:1999), and in some circumstances for as long as 27 months. *The Laryngoscope* 109:1344-1346:1999. However, the usual duration of an intramuscular injection of Botox® is typically about 3 to 4 months.

A commercially available botulinum toxin containing pharmaceutical composition is sold under the trademark BOTOX® (available from Allergan, Inc., of Irvine, Calif.). BOTOX® consists of a purified botulinum toxin type A complex, human serum albumin, and sodium chloride packaged in sterile, vacuum-dried form. The botulinum toxin type A is made from a culture of the Hall strain of *Clostridium botulinum* grown in a medium containing N-Z amine casein and yeast extract. The botulinum toxin type A complex is purified from the culture solution by a series of acid or acid and ethanol precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. BOTOX® can be reconstituted with sterile, non-preserved saline prior to intramuscular injection. Each vial of BOTOX® contains about 100 units (U) of *Clostridium botulinum* toxin type A complex, 0.5 milligrams of human serum albumin and 0.9 milligrams of sodium chloride in a sterile, vacuum-dried form without a preservative.

To reconstitute vacuum-dried BOTOX® sterile normal saline without a preservative (0.9% Sodium Chloride injection) is used by drawing up the proper amount of diluent in the appropriate size syringe. Since BOTOX® is denatured by bubbling or similar violent agitation, the diluent is gently injected into the vial. Reconstituted BOTOX® can be stored in a refrigerator (2° to 8° C.) and is a clear, colorless liquid and free of particulate matter. There are reports of reconstituted BOTOX® retaining its potency for up to thirty days. See e.g. Guttman C., *Botox retains its efficacy for blepharospasm treatment after freezing and storage, New York investigators find*, EuroTimes 2000 November/December; 5(8):16. The vacuum-dried product is stored in a freezer at or below −5° C.

In general, four physiologic groups of *C. botulinum* are recognized (I, II, III, IV). The organisms capable of producing a serologically distinct toxin may come from more than one physiological group. For example, Type B and F toxins can be produced by strains from Group I or II. In addition, other strains of clostridial species (*C. baratii*, type F; *C. butyricum*, type E; *C. novyi*, type $C_1$ or D) have been identified which can produce botulinum neurotoxins.

The physiologic groups of *Clostridium botulinum* types are listed in Table I.

TABLE I

Physiologic Groups of *Clostridium botulinum*

| Group | Toxin Sero-Type | Biochemistry | Milk Digest | Glucose Fermentation | Lipase | Phages & Plasmids | Phenotypically Related *Clostridium* (nontoxigenic) |
|---|---|---|---|---|---|---|---|
| I | A, B, F | proteolytic saccharolytic | + | + | + | + | *C. sporogenes* |
| II | B, E, F | nonproteolytic saccharolytic psychotrophic | − | + | + | + | |
| III | C, D | Nonproteolytic saccharolytic | ± | + | + | + | *C. novyi* |
| IV | G | proteolytic nonsaccharolytic | + | − | − | − | *C. subterminale* |

These toxin types may be produced by selection from the appropriate physiologic group of *Clostridium botulinum* organisms. The organisms designated as Group I are usually referred to as proteolytic and produce botulinum toxins of types A, B and F. The organisms designated as Group II are saccharolytic and produce botulinum toxins of types B, E and F. The organisms designated as Group III produce only botulinum toxin types C and D and are distinguished from organisms of Groups I and II by the production of significant amounts of propionic acid. Group IV organisms produce only neurotoxin of type G.

It is known to obtain a tetanus toxin using specific media substantially free of animal products. See e.g. U.S. Pat. No. 6,558,926. But notably, even the "animal product free" media disclosed by this patent uses Bacto-peptone, a meat digest. Significantly, production of tetanus toxin by *Clostridium tetani* vs. production of a botulinum toxin by a *Clostridium botulinum* bacterium entails different growth, media and fermentation parameters and considerations. See e.g. Johnson, E. A., et al., *Clostridium botulinum* and its neurotoxins: a metabolic and cellular perspective, Toxicon 39 (2001), 1703-1722.

Production of Active Botulinum Neurotoxin

Botulinum toxin for use in a pharmaceutical composition can be obtained by anaerobic fermentation of *Clostridium botulinum* using a modified version of the well known Schantz process (see e.g. Schantz E. J., et al., *Properties and use of botulinum toxin and other microbial neurotoxins in medicine*, Microbiol Rev 1992 March; 56(1):80-99; Schantz E. J., et al., *Preparation and characterization of botulinum toxin type A for human treatment*, chapter 3 in Jankovic J, ed. *Neurological Disease and Therapy. Therapy with botulinum toxin* (1994), New York, Marcel Dekker; 1994, pages 41-49, and; Schantz E. J., et al., *Use of crystalline type A botulinum toxin in medical research*, in: Lewis G E Jr, ed. *Biomedical Aspects of Botulism* (1981) New York, Academic Press, pages 143-50.).

A *Clostridium botulinum* neurotoxin (as pure toxin or as a botulinum toxin complex) can also be obtained by aerobic fermentation of a recombinant host cell which bears the appropriate gene. See e.g. U.S. Pat. No. 5,919,665 entitled Vaccine for *clostridium botulinum* neurotoxin, issued Jul. 6, 1999 to Williams and U.S. patent application 20030215468 entitled Soluble recombinant botulinum toxin proteins by Williams et al., published Nov. 20, 2003.

Additionally, botulinum toxins (the 150 kilodalton molecule) and botulinum toxin complexes (300 kDa to 900 kDa) can be obtained from, for example, List Biological Laboratories, Inc., Campbell, Calif.; the Centre for Applied Microbiology and Research, Porton Down, U.K.; Wako (Osaka, Japan), as well as from Sigma Chemicals of St Louis, Mo. Commercially available botulinum toxin containing pharmaceutical compositions include Botox® (Botulinum toxin type A purified neurotoxin complex with human serum albumin and sodium chloride) available from Allergan, Inc., of Irvine, Calif. in 100 unit vials as a lyophilized powder to be reconstituted with 0.9% sodium chloride before use), Dysport® (*Clostridium botulinum* type A toxin hemagglutinin complex with human serum albumin and lactose in the botulinum toxin pharmaceutical composition), available from Ipsen Limited, Berkshire, U.K. as a powder to be reconstituted with 0.9% sodium chloride before use), and MyoBloc™ (an injectable solution comprising botulinum toxin type B, human serum albumin, sodium succinate, and sodium chloride at about pH 5.6, available from Solstice Neurosciences (formerly available from Elan Corporation, Dublin, Ireland) of San Diego, Calif.

A number of steps are required to make a Clostridial toxin pharmaceutical composition suitable for administration to a human or animal for a therapeutic, diagnostic, research or cosmetic purpose. These steps can include obtaining a purified Clostridial toxin and then compounding the purified Clostridial toxin. A first step can be to culture a Clostridial bacteria, typically on agar plates, in an environment conducive to bacterial growth, such as in a warm anaerobic atmosphere. The culture step allows Clostridial colonies with desirable morphology and other characteristics to be obtained. In a second step selected cultured Clostridial colonies can be fermented in a suitable medium. After a certain period of fermentation the Clostridial bacteria typically lyse and release Clostridial toxin into the medium. Thirdly, the culture medium can be purified so as to obtain a bulk or raw toxin. Typically culture medium purification to obtain bulk toxin is carried out using, among other reagents, animal derived enzymes, such as DNase and RNase, which are used to degrade and facilitate removal of nucleic acids. The resulting bulk toxin can be a highly purified toxin with a high specific activity. After stabilization in a suitable buffer, the bulk toxin can be compounded with one or more excipients to make a Clostridial toxin pharmaceutical composition suitable for administration to a human. The Clostridial toxin pharmaceutical composition can comprises a Clostridial toxin as an active pharmaceutical ingredient. The pharmaceutical composition can also include one or more excipients, buffers, carriers, stabilizers, preservatives and/or bulking agents.

The *Clostridium* toxin fermentation step can result in a culture solution which contains whole *Clostridium* bacteria, lysed bacteria, culture media nutrients and fermentation byproducts. Filtration of this culture solution so as to remove gross elements, such as whole and lysed bacteria, provides a clarified culture. The clarified culture solution comprises a Clostridial and various impurities and can be processed so as to obtain a concentrated Clostridial toxin, which is called bulk toxin.

Fermentation and purification processes for obtaining a bulk Clostridial toxin using one or more animal derived products (such as the milk digest casein, DNase and RNase) are known. An example of such a known non-APF process for obtaining a botulinum toxin complex is the Schantz process. The Schantz process (from initial cell culture through to fermentation and toxin purification) makes use of a number of products derived from animal sources such as for example animal derived Bacto Cooked Meat medium in the culture vial, Columbia Blood Agar plates for colony growth and selection, and casein in the fermentation media. Additionally, the Schantz bulk toxin purification process makes use of DNase and RNase from bovine sources to hydrolyze nucleic acids present in the toxin containing fermented culture medium.

A fermentation process for obtaining a tetanus toxoid which uses reduced amounts of animal derived products (referred to as animal protein free or "APF" fermentation processes) is known. See e.g. U.S. Pat. No. 6,558,926 entitled Method for production of tetanus toxin using media substantially free of animal products, issued to Demain et al., May 6, 2003. An APF fermentation process for obtaining a Clostridial toxin, has the potential advantage of reducing the (the already very low) possibility of contamination of the ensuing bulk toxin with viruses, prions or other undesirable elements which can then accompany the active pharmaceutical ingredient Clostridial toxin as it is compounded into a pharmaceutical composition for administration to humans.

It is known to use chromatography to purify a Clostridial toxin. Thus:
1. Ozutsumi K., et al, *Rapid, simplified method for production and purification of tetanus toxin*, App & Environ Micro, April 1985, p 939-943, vol 49, no. 4. (1985) discloses use of high pressure liquid chromatography (HPLC) gel filtration to purify tetanus toxin.
2. Schmidt J. J., et al., *Purification of type E botulinum neurotoxin by high-performance ion exchange chromatography*, Anal Biochem 1986 July; 156(1):213-219 discloses use of size exclusion chromatography or ion exchange chromatograph to purify botulinum toxin type E. Also disclosed is use of protamine sulfate instead of ribonuclease (RNase).
3. Simpson L. L., et al., *Isolation and characterization of the botulinum neurotoxins* Simpson L L; Schmidt J J; Middlebrook J L, In: Harsman S, ed. *Methods in Enzymology*. Vol. 165, *Microbial Toxins: Tools in Enzymology* San Diego, Calif.: Academic Press; vol 165:pages 76-85 (1988) discloses purification of botulinum neurotoxins using gravity flow chromatography, HPLC, capture steps using an affinity resin, size exclusion chromatography, and ion (anion and cation) exchange chromatography, including use of two different ion exchange columns. Various Sephadex, Sephacel, Trisacryl, S and Q columns are disclosed.
4. Zhou L., et al., *Expression and purification of the light chain of botulinum neurotoxin A: A single mutation abolishes its cleavage of SNAP-25 and neurotoxicity after reconstitution with the heavy chain*, Biochemistry 1995; 34(46):15175-81 (1995) discloses use of an amylose affinity column to purify botulinum neurotoxin light chain fusion proteins.
5. Kannan K., et al., *Methods development for the biochemical assessment of Neurobloc (botulinum toxin type B)*, Mov Disord 2000; 15(Suppl 2):20 (2000) discloses use of size exclusion chromatography to assay a botulinum toxin type B.
6. Wang Y-c, *The preparation and quality of botulinum toxin type A for injection (BTXA) and its clinical use*, Dermatol Las Faci Cosm Surg 2002; 58 (2002) discloses ion exchange chromatography to purify a botulinum toxin type A. This reference discloses a combination of precipitation and chromatography techniques.
7. Johnson S. K., et al., *Scale-up of the fermentation and purification of the recombination heavy chain fragment C of botulinum neurotoxin serotype F, expressed in Pichia pastoris*, Protein Expr and Purif 2003; 32:1-9 (2003) discloses use of ion exchange and hydrophobic interaction columns to purify a recombinant heavy chain fragment of a botulinum toxin type F.
8. Published U.S. patent application 2003 0008367 A1 (Oguma) discloses use of ion exchange and lactose columns to purify a botulinum toxin.

The purification methods summarized above relate generally to research or laboratory scale methods which are not scaleable into industrial or commercial processes. It is well known that chromatography techniques such as, for example, gel filtration and gravity flow chromatography are not amenable for use as large-scale, validatable, cGMP manufacturing processes. Alternately or in addition, the purification method summarized above relate to small scale purification of the pure toxin (i.e. the approximately 150 kDa neurotoxic molecule), or a specific component of the neurotoxic, as opposed of the entire 900 kDa botulinum toxin complex. As is also well known, obtaining a biologically active, purified botulinum toxin complex is considerably more complex and difficult, than is purifying only a component of the complex. This is due, for example, to the larger size, fragility, labile nature and particular secondary, tertiary and quaternary molecule and complex conformations required for obtaining a biologically active and stable botulinum toxin complex.

Furthermore, existing processes, including commercial scale processes, for obtaining a botulinum toxin suitable for compounding into a botulinum toxin pharmaceutical composition typically include a series of precipitation steps to separate the toxin complex from impurities which accompany the botulinum toxin from the fermentation process. Notably, precipitation techniques are widely used in the biopharmaceutical industry to purify a botulinum toxin. For example, cold alcohol fractionation (Cohn's method) or precipitation is used to remove plasma proteins. Unfortunately, precipitation techniques for purifying a botulinum toxin have the drawbacks of low resolution, low productivity, difficulty to operate, difficulty to control and/or validate, and difficulty to scale-up or scale-down.

What is needed therefore is an APF process for purifying a Clostridial toxin fermentation medium so as to obtain a bulk Clostridial toxin without making use of animal derived products in the purification process.

SUMMARY

Our invention provides various chromatographic APF systems and processes for purifying a Clostridial toxin. The systems and processes of our invention are scalable and cGMP compliant. The Clostridial toxin is preferably a botulinum toxin, and most preferably a botulinum toxin type A 900 kDa complex. The present invention can be used as a commercial, industrial scale APF purification process, to purify the Clostridial toxin (such as botulinum toxin) obtained from a separate APF fermentation (i.e. use of soy instead of casein in the fermentation medium) of a Clostridial bacterium. The present invention therefore permits replacement of the non-APF purification (i.e. use of DNase and RNase) process, which is typically carried out after a non-APF fermentation, to purify the botulinum toxin.

The present invention can also have utility subsequent to a Schantz fermentation of a Clostridial bacterium, to replace the Schantz (non-APF) purification process, with the herein disclosed APF toxin purification process. It is not preferred to practice the present invention after a non-APF fermentation process, as opposed to practicing the present invention after an APF fermentation process, because the present invention has been optimized for use subsequent to an APF fermentation process.

Thus, processes within the scope of the present invention are preferably used in conjunction with (subsequent to) an APF fermentation to thereby further reduce, and in certain embodiments eliminate, use of animal derived products in the steps required to obtain a bulk Clostridial toxin. Clearly practice of the present invention subsequent to an APF fermentation process permits an essentially completely APF methodology (fermentation and purification) to be carried out.

An embodiment of the present invention provides a system and process for obtaining high yield of highly purified biologically active Clostridial toxin. The present invention accomplishes this through use of a free or substantially animal product free chromatographic system and process to purify a clarified culture obtained from the fermentation processes of a *Clostridium* bacterium, such as a *Clostridium botulinum* bacterium.

DEFINITIONS

As used herein, the words or terms set forth below have the following definitions.

"About" means that the item, parameter or term so qualified encompasses a range of plus or minus ten percent above and below the value of the stated item, parameter or term.

"Administration," or "to administer" means the step of giving (i.e. administering) a pharmaceutical composition to a subject. The pharmaceutical compositions disclosed herein are "locally administered" by e.g. intramuscular (i.m.), intradermal, subcutaneous administration, intrathecal administration, intracranial. intraperitoneal (i.p.) administration, topical (transdermal) and implantation (i.e. of a slow-release device such as polymeric implant or miniosmotic pump) routes of administration.

"Animal product free" or "substantially animal product free" encompasses, respectively, "animal protein free" or "substantially animal protein free" and means the absence or substantial absence of blood derived, blood pooled and other animal derived products or compounds. "Animal" means a mammal (such as a human), bird, reptile, fish, insect, spider or other animal species. "Animal" excludes microorganisms, such as bacteria. Thus, an animal product free medium or process or a substantially animal product free medium or process within the scope of the present invention can include a botulinum toxin or a Clostridial botulinum bacterium. For example, an animal product free process or a substantially animal product free process means a process which is either substantially free or essentially free or entirely free of animal derived proteins, such as immunoglobulins, meat digest, meat by products and milk or dairy products or digests. Thus, an example of an animal product free process is a process (such as a bacterial culturing or bacterial fermentation process) which excludes meat and dairy products or meat or dairy by products.

"Botulinum toxin" means a neurotoxin produced by *Clostridium botulinum*, as well as modified, recombinant, hybrid and chimeric botulinum toxins. A recombinant botulinum toxin can have the light chain and/or the heavy chain thereof made recombinantly by a non-Clostridial species. "Botulinum toxin," as used herein, encompasses the botulinum toxin serotypes A, B, C, D, E, F and G. "Botulinum toxin," as used herein, also encompasses both a botulinum toxin complex (i.e. the 300, 600 and 900 kDa complexes) as well as pure botulinum toxin (i.e. the about 150 kDa neurotoxic molecule), all of which are useful in the practice of the present invention. "Purified botulinum toxin" means a pure botulinum toxin or a botulinum toxin complex that is isolated, or substantially isolated, from other proteins and impurities which can accompany the botulinum toxin as it is obtained from a culture or fermentation process. Thus, a purified botulinum toxin can have at least 90%, preferably more than 95%, and most preferably more than 99% of the non-botulinum toxin proteins and impurities removed. The botulinum $C_2$ and $C_3$ cytotoxins, not being neurotoxins, are excluded from the scope of the present invention.

"Clostridial neurotoxin" means a neurotoxin produced from, or native to, a Clostridial bacterium, such as *Clostridium botulinum*, *Clostridium butyricum* or *Clostridium beratti*, as well as a Clostridial neurotoxin made recombinantly by a non-Clostridial species.

"Entirely free" (i.e. "consisting of" terminology) means that within the detection range of the instrument or process being used, the substance cannot be detected or its presence cannot be confirmed.

"Essentially free" (or "consisting essentially of") means that only trace amounts of the substance can be detected.

"Modified botulinum toxin" means a botulinum toxin that has had at least one of its amino acids deleted, modified, or replaced, as compared to a native botulinum toxin. Additionally, the modified botulinum toxin can be a recombinantly produced neurotoxin, or a derivative or fragment of a recombinantly made neurotoxin. A modified botulinum toxin retains at least one biological activity of the native botulinum toxin, such as, the ability to bind to a botulinum toxin receptor, or the ability to inhibit neurotransmitter release from a neuron. One example of a modified botulinum toxin is a botulinum toxin that has a light chain from one botulinum toxin serotype (such as serotype A), and a heavy chain from a different botulinum toxin serotype (such as serotype B). Another example of a modified botulinum toxin is a botulinum toxin coupled to a neurotransmitter, such as substance P.

"Patient" means a human or non-human subject receiving medical or veterinary care. Accordingly, as disclosed herein, the compositions may be used in treating any animal, such as mammals.

"Pharmaceutical composition" means a formulation in which an active ingredient can be a botulinum toxin. The word "formulation" means that there is at least one additional ingredient (such as an albumin and/or sodium chloride) in the pharmaceutical composition besides a neurotoxin active ingredient. A pharmaceutical composition is therefore a formulation which is suitable for diagnostic, therapeutic or cosmetic administration (i.e. by intramuscular or subcutaneous injection or by insertion of a depot or implant) to a subject, such as a human patient. The pharmaceutical composition can be: in a lyophilized or vacuum dried condition; a solution formed after reconstitution of the lyophilized or vacuum dried pharmaceutical composition with saline or water, or; as a solution which does not require reconstitution. The active ingredient can be one of the botulinum toxin serotypes A, B, $C_1$, D, E, F or G or a botulinum toxin, all of which can be made natively by Clostridial bacteria. As stated, a pharmaceutical composition can be liquid or solid, for example vacuum-dried. The constituent ingredients of a pharmaceutical composition can be included in a single composition (that is all the constituent ingredients, except for any required reconstitution fluid, are present at the time of initial compounding of the pharmaceutical composition) or as a two-component system, for example a vacuum-dried composition reconstituted with a diluent such as saline which diluent contains an ingredient not present in the initial compounding of the pharmaceutical composition. A two-component system provides the benefit of allowing incorporation of ingredients which are not sufficiently compatible for long-term shelf storage with the first component of the two component system. For example, the reconstitution vehicle or diluent may include a preservative which provides sufficient protection against microbial growth for the use period, for example one-week of refrigerated storage, but is not present during the two-year freezer storage period during which time it might degrade the toxin. Other ingredients, which may not be compatible with a Clostridial toxin or other ingredients for long periods of time, may be incorporated in this manner; that is, added in a second vehicle (i.e. in the reconstitution fluid) at the approximate time of use. Methods for formulating a botulinum toxin active ingredient pharmaceutical composition are disclosed in U.S. patent publication 2003 0118598 A1.

"Substantially free" means present at a level of less than one percent by weight of the pharmaceutical composition.

"Therapeutic formulation" means a formulation can be used to treat and thereby alleviate a disorder or a disease, such as a disorder or a disease characterized by hyperactivity (i.e. spasticity) of a peripheral muscle.

The following abbreviations are used herein:

3:1:1 culture a botulinum toxin culture/fermentation medium containing 3% HySoy, 1% HyYeast, and 1% glucose. HySoy (Quest product no. 5X59022) is a source of peptides made by enzymatic hydrolysis of soy. HyYeast (HyYest, Quest product no. 5Z10102 or 5Z10313 is a baker's yeast extract.

5:1:1 culture a botulinum toxin culture/fermentation medium containing 5% HySoy, 1% HyYeast, and 1% glucose.

API active pharmaceutical ingredient

APF animal product free

BCA bicinchoninic acid

CV column volume

DF diafiltration

ELISA enzyme linked immunosorbent assay. "Hc" in "Hc-ELISA means a botulinum toxin heavy chain.

MLD50 the amount of a botulinum toxin which is a lethal dose to 50% of 18-23 gram Swiss-Weber mice injected intraperitoneally SDS-PAGE sodium dodecylsulfate-polyacrylamide gel electrophoresis SEC-HPLC size exclusion high performance liquid chromatography UF ultrafiltration UV ultraviolet Our invention includes a process for purifying a Clostridium toxin. The process can have the four steps of obtaining a sample of a botulinum toxin fermentation culture; contacting a first chromatography column resin with the culture sample so as to permit capture of a botulinum toxin by the first column; eluting the botulinum toxin from the first column, and; loading a second column chromatography column resin with the eluent from the first chromatography column, thereby obtaining a purified botulinum toxin. By "botulinum toxin fermentation culture" it is meant a fermentation medium in which a Clostridium botulinum bacterium has been fermented so that the bacterium has released botulinum toxin into the medium. The sample of a botulinum toxin fermentation culture (medium) is preferably a sample of a clarified culture of the fermentation medium.

The first chromatography column and the second chromatography column can be different columns, and the two different columns can act to purify a botulinum toxin through different purification mechanisms. For example, the first chromatography column can be a hydrophobic interaction column and the second chromatography column can be an ion exchange column.

A process for purifying a Clostridium toxin within the scope of our invention can also have the step after the contacting step and before the eluting step, of washing impurities off the first column. Additionally, a process for purifying a Clostridium toxin within the scope of our invention can also have the step after the loading step, the step of washing impurities off the second column. Furthermore, a process for purifying a Clostridium toxin within the scope of our invention can also have, after the step of washing impurities off the second column, the step of eluting the botulinum toxin from the second column.

Preferably, a process for purifying a Clostridium toxin within the scope of our invention is an APF process, more preferably it is a substantially animal protein free ("APF") process, and more preferably it is an essentially APF process for purifying a clostridial toxin, such as a botulinum toxin complex.

The botulinum toxin fermentation culture used in a process for purifying a Clostridium toxin within the scope of our invention preferably results from an APF process, more preferably results from a substantially APF process, and most preferably results from an essentially APF process.

Significantly, a process for purifying a Clostridium toxin within the scope of our invention can provide a yield of purified botulinum toxin complex greater than about 50 mg per batch for each 10 liters of the botulinum toxin fermentation culture.

A purified botulinum toxin complex obtained by practice of a process for purifying a Clostridium toxin within the scope of our invention can have the following characteristics: an appearance as an white to off-white suspension; a concentration of 2.0-3.6 mg of botulinum toxin complex per ml of eluent; the ratio of absorbance at 260 nm to absorbance at 278 nm (A260/A278) is less than or equal to 0.6; a specific potency in MLD50 unit/mg of between $2.4 \times 10^7$ to $5.9 \times 10^7$ MLD50 units per mg of the purified botulinum toxin; an immunological identity to botulinum neurotoxin type A complex; an SDS-PAGE characteristic that conforms to standard; an SEC-HPLC characteristic of 900 kDa toxin complex of >95% of the total peak, and; the process used to obtain such a purified botulinum toxin complex is robust, scalable, validatable, and/or cGMP compliant.

An APF process for purifying a botulinum toxin complex within the scope of our invention can have the steps of:

(a) obtaining a sample of a botulinum toxin fermentation culture, wherein the botulinum toxin fermentation culture results from a substantially APF process.

(b) contacting a hydrophobic interaction chromatography column resin with the culture sample so as to permit capture of a botulinum toxin by the first column;

(c) washing impurities off the hydrophobic interaction chromatography column;

(d) eluting the botulinum toxin from the hydrophobic interaction column (the eluting step can be followed by the step of diluting the eluent from the hydrophobic interaction chromatography column for a subsequent ion exchange chromatography);

(e) loading an ion exchange column chromatography column resin with the eluent (such as the diluted eluent from the hydrophobic interaction chromatography column) from the hydrophobic interaction chromatography column;

(f) washing impurities off the ion exchange chromatography column, and;

(g) eluting the botulinum toxin from the ion change column, thereby obtaining a purified botulinum toxin through a process for purifying a botulinum toxin which is a substantially APF purification process.

The APF process set forth in the paragraph above can further comprise, after the step of obtaining a sample of a botulinum toxin fermentation culture and before the step of contacting a hydrophobic interaction chromatography column resin with the culture sample, the additional step of conditioning the clarified culture for hydrophobic interaction chromatography. Additionally, the APF process set forth in the paragraph above can further comprise, after the step of eluting the botulinum toxin from the hydrophobic interaction column and before the step of loading an ion exchange column chromatography column resin with the eluent from the hydrophobic interaction chromatography column, the step of conditioning the eluent from hydrophobic interaction column for ion exchange chromatography.

A detailed embodiment of an APF process for purifying a botulinum toxin, the process can comprise the steps of:

(a) obtaining a sample of a botulinum toxin fermentation culture, wherein the botulinum toxin fermentation culture results from a substantially APF process.

(b) conditioning the clarified culture for hydrophobic interaction chromatography;

(c) contacting a hydrophobic interaction chromatography column resin with the culture sample so as to permit capture of a botulinum toxin by the first column;

(d) washing impurities off the hydrophobic interaction chromatography column;

(e) eluting the botulinum toxin from the hydrophobic interaction column;

(f) conditioning the eluent from hydrophobic interaction column for ion exchange chromatography;

(g) loading an ion exchange column chromatography column resin with the conditioned eluent from the hydrophobic interaction chromatography column;

(h) washing impurities off the ion exchange chromatography column, and;

(i) eluting the botulinum toxin from the ion change column, thereby obtaining a purified botulinum toxin through a process for purifying a botulinum toxin which is a substantially APF purification process.

Also within the scope of our invention is a system for purifying a *Clostridium* toxin, such as a botulinum toxin type A complex. Such a system can comprise: a first chromatography column resin for capturing a botulinum toxin from a fermentation culture; an elution buffer for eluting the botulinum toxin from the first column; a second column chromatography column resin for capturing a botulinum toxin from an eluent from the first chromatography column, and; a second elution buffer for eluting the botulinum toxin from the second chromatography column.

DRAWINGS

Aspects of the invention are explained or illustrated by the following drawings.

FIG. 1 entitled N-Source (i.e. HySoy plus YE) % vs. Potency and pH" is a graph showing botulinum toxin activity as determined: (1) on the left side Y axis as mouse lethal dose 50 (MLD 50), and; (2) on the left side Y axis as SNAP 25 activity, of various APF media at the elapsed fermentation times shown at the top of the bars, for APF medium pH as shown on the right side Y axis the pH, for APF media with the wt % amount of hydrolyzed soy concentrate and yeast extract concentrate as shown by the X axis. All FIG. 1 media also contained 1% by wt glucose.

FIG. 2 is a summary flow chart comparing a non-APF process for obtaining a botulinum toxin (the top half of FIG. 2) with an APF process, within the scope of the present invention, for obtaining a botulinum toxin (the bottom half of FIG. 2), through the cell bank creation, culture and fermentation steps. FIG. 2 omits the harvest and purification steps.

FIG. 3 is a chromatograph obtained from hydrophobic interaction chromatography of an APF clarified culture (a 3.1.1 culture) on a Butyl Sepharose Fast Flow column. The X axis in FIG. 3 represents the volume in ml of liquid (effluent) which has passed through the column. The Y axis represents absorbance at 280 nm in mAU.

FIG. 4 is a chromatograph obtained from ionic exchange chromatography of the eluent from the FIG. 3 Butyl column on an SP Sepharose high performance column. The axes in FIG. 4 are the same as they are for FIG. 3.

FIG. 5A is an image of reduced SDS-PAGE of various fractions obtained from operation of the Butyl column of FIG. 3. The left hand side of FIG. 5A is marked vertically with descending molecular weights in thousands of Daltons (kDa). The numbers 1 to 8 along the bottom border of FIG. 5A represents the lanes in which fractions were loaded.

Figure 8:
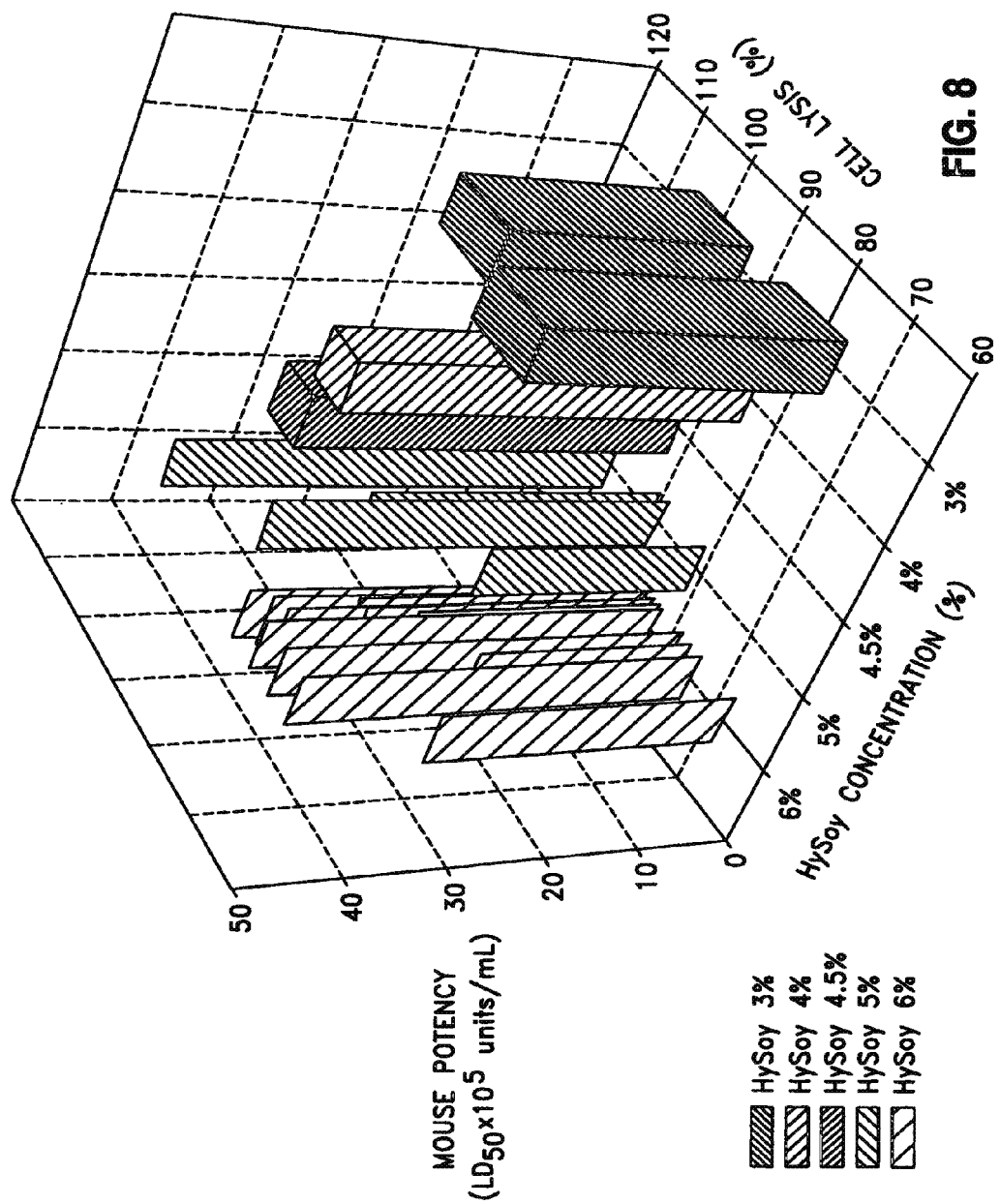

FIG. 8 is a graph comparing the effect of a soy protein concentration on a botulinum toxin type A complex production in an APF fermentation process, where the fermentation medium contained 1 wt % glucose and 1 wt % of a yeast extract. In FIG. 8 the X axis represents the weight percent concentration in the fermentation medium of a particular hydrolyzed soy protein (HySoy), the left side Y axis represents potency of the final purified botulinum toxin complex and the right side Y axis represents the percent of cell lysis completed, as determined by the equation:

$$\text{Cell Lysis } (\%) = \frac{OD_{600 \ max} - OD_{600 \ endpoint}}{OD_{600 \ max}} \times 100$$

where $OD_{600\ max}$ corresponds to the optical density measured at 600 nm at the time of maximum growth, and $OD_{600\ endpoint}$ is at the time of fermentation harvest.

DESCRIPTION

The present invention is based upon the discovery that a Clostridial toxin can be purified by use of an animal product fee (APF) system and process. The present invention encompasses a animal product free system and process for purifying a *Clostridium botulinum* neurotoxin. The *Clostridium botulinum* neurotoxin can be a botulinum toxin type A complex, such as a 300 kD, 500 kD or 900 kD (approximate molecular weights) complex or mixtures thereof. The *Clostridium botulinum* neurotoxin can be any one of the serotypes A, B, C, D, E, F or G or mixtures thereof. Additionally, the system and process can be practiced in conjunction with a recombinant, hybrid, chimeric or modified botulinum toxin (light chain, heavy chain, or both chains together).

Significantly, the system and process disclosed herein is scalable, meaning that it can be used to purify the quantities of botulinum toxin obtained from an industrial or commercial process, as use for pharmaceutical production. Further, the system and process is also CGMP (certified good manufacturing practices) compliant, as required by the U.S. CFR (United States code of federal regulations), meaning that it can comply with regulatory requirements.

Through experimentation, there were developed APF systems and processes to purify a Clostridial toxin, such as a *Clostridium botulinum* type A (Hall strain) neurotoxin complex. The Clostridial toxin is purified from the fermentation medium resulting from either a Schantz (non-APF) fermentation process or from an APF fermentation process. Schantz processes use animal derived products. Significantly, while an APF fermentation process can reduce or eliminate animal derived products (such as casein and meat broth) as nutrients from the media used to culture and ferment Clostridial bacteria, APF fermentation processes are typically followed by one or more purification steps which make use of animal derived products, such as the enzymes DNase and RNase. Purification of the fermentation medium is required to obtain bulk Clostridial toxin. Bulk Clostridial toxin (pure toxin or toxin complex) can be used for compounding a Clostridial toxin pharmaceutical composition.

Preferably, the present invention is practiced in conjunction with an APF fermentation process. Practicing the present invention in conjunction with an APF fermentation process provides a combined APF fermentation process and an APF purification process. Additionally, systems and method of the present invention are optimized for operation upon an APF fermentation medium, as opposed to a casein or other animal protein based fermentation medium. Practicing the presently invention upon a non-APF fermentation can result in a lower yield and/or a lower potency of the purified botulinum toxin obtained.

Thus, although both the Schantz and APF botulinum toxin purification processes use animal derived products such as benzamidine to stabilize the botulinum toxin and DNase and RNase to remove nucleic acids present with the botulinum toxin in the fermentation medium (see e.g. Examples 6 and 7), our invention permits a botulinum toxin can be purified without using such animal derived products.

The present invention encompasses systems and processes for purifying a Clostridial toxin, such as a botulinum toxin complex. Typically a particular system within the scope of the present invention is operated in conjunction with a particular process within the scope of the present invention. A system within the scope of the present invention can comprise a plurality (preferably as a consecutive series) of chromatography steps. A process within the scope of the present invention can comprise passing a Clostridial toxin fermentation medium through the plurality of chromatography columns to thereby obtain a highly purified and highly potent Clostridial toxin. Such a purified Clostridial toxin is suitable for compounding a Clostridial toxin pharmaceutical composition. Important parameters of systems and processes within the scope of the present invention include the particular columns, buffers and operating (column running) conditions used.

A first broad step of In a particular embodiment of the invention can be to load a fermentation medium clarified culture onto a hydrophobic interaction column (such as a Butyl Sepharose Fast Flow ["FF"] column). This first column captures the Clostridial toxin (such as a botulinum toxin complex) and allows impurities to flow through the column. It was found that a hydrophobic interaction column provided an efficient capture of a botulinum toxin complex (a large protein with a particular tertiary and quaternary structure) from fermentation medium with retention of the biological activity of the botulinum toxin complex, while also separating (flow through) of many impurities present with the botulinum toxin in the fermentation medium. A suitable buffer is used to elute the captured (bound) Clostridial toxin from the hydrophobic interaction column.

In a second broad step in a particular embodiment of the present invention, the eluent from the first column is loaded onto a second column to further purify the Clostridial toxin. It was found that preferably, if second column [provides a different mechanism for separation of Clostridial toxin from impurities, then a second column chromatography step can provide a further efficient purification step. Thus, preferably, the second chromatography step entails use of a different column, such as a SP Sepharose high performance ["HP"] column.

In post chromatography (column) steps eluent from the second column can then be further processed to obtain highly purified bulk botulinum toxin complex. These additional processing steps can include buffer exchange by ultrafiltration and diafiltration, sterile filtration and preparation of an ammonium sulphate suspension of the purified botulinum toxin complex.

Our invention encompasses a scalable and cGMP compliant system and process for purifying a botulinum toxin, which can result in obtaining a bulk botulinum toxin with the characteristics set forth in Table 1.

TABLE 1

| Purified Botulinum Neurotoxin Characteristics | |
|---|---|
| Appearance | White to off-white suspension |
| Concentration | 2.0-3.6 mg/ml |
| Nucleic Acids (A260/A278) | Not more than 0.6 |
| Specific Potency (MLD50 unit/mg) | $2.4\text{-}5.9 \times 10^7$ |
| Immunological Identity | Pass |
| SDS-PAGE | Conformed to standard |
| SEC-HPLC | 900 kDa toxin complex >95% total peak |

A commercially available botulinum toxin containing pharmaceutical composition is sold under the trademark BOTOX® (available from Allergan, Inc., of Irvine, Calif.). BOTOX® has the characteristics set forth in Table 1 above. BOTOX® consists of a purified botulinum toxin type A complex, human serum albumin, and sodium chloride packaged in sterile, vacuum-dried form. The botulinum toxin type A is made from a culture of the Hall strain of *Clostridium botulinum* grown in a medium containing N-Z amine casein and yeast extract (i.e. non-APF process). The botulinum toxin type A complex is purified from the culture solution by a series of precipitation (including acid precipitation) steps to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. BOTOX® can be reconstituted with sterile, non-preserved saline prior to intramuscular injection. Each vial of BOTOX® contains about 100 units (U) of *Clostridium botulinum* toxin type A complex, 0.5 milligrams of human serum albumin and 0.9 milligrams of sodium chloride in a sterile, vacuum-dried form without a preservative.

To reconstitute vacuum-dried BOTOX® sterile normal saline without a preservative (0.9% Sodium Chloride injection) is used by drawing up the proper amount of diluent in the appropriate size syringe. Since BOTOX® is denatured by bubbling or similar violent agitation, the diluent is gently injected into the vial. It has been reported that BOTOX® has been administered thirty or more days after reconstitution with little loss of potency. During this time period, reconstituted BOTOX® is stored in a refrigerator (2° to 8° C.). Reconstituted BOTOX® is clear, colorless and free of particulate matter. The vacuum-dried product is stored in a freezer at or below −5° C.

The present invention is based upon the discovery of media and processes which are free or substantially free of an animal product or an animal byproduct useful for culture and fermentation of an organism (such as a *Clostridium botulinum* bacterium) capable of producing biologically active botulinum toxin. The botulinum toxin obtained can be used for making botulinum toxin active ingredient pharmaceutical compositions. Thus, growth media are disclosed herein which have significantly reduced levels of meat or dairy by-products and preferred media embodiments are substantially free of such animal products.

The present invention encompasses the surprising finding that animal-based products are not required in media for growth of *Clostridium botulinum*, and particularly that vegetable-based products can replace animal-based products typically employed in such media for the growth of *Clostridium botulinum*.

Media that are in current use for growth and fermentation of bacteria usually comprise one or more animal derived ingredients, such as coked meat. In accordance with the present invention, preferred media for growth of *Clostridium botulinum* contain anima derived ingredients which comprise no more than about five to about ten percent of the total weight of the media. More preferably, media within the scope of the invention comprise no more than about one to less than about five percent of the total weight of the media of anima-derived products. Most preferably, all media and cultures used for the growth of *Clostridium botulinum* for the production of botulinum toxin are completely free of animal derived products. These media include but are not limited to media for small and large scale fermentation of *Clostridium botulinum*, media for growth of cultures of *Clostridium botulinum* used to inoculate the seed (first) media and fermentation (second) media, as well as and media used for long-term storage of cultures of *Clostridium botulinum* (e.g. stock cultures).

In certain preferred embodiments of the invention, the media for the growth of *Clostridium botulinum* and production of botulinum toxin can comprise soy based products to replace animal derived products. Alternately, instead of a soy based product there can be used debittered seed of *Lupinus campestris*. It is known the protein content of *L. campestris* seed is very similar to that of soybean. Preferably, these media include soybean or of *L. campestris* derived products that are hydrolyzed and that are soluble in water. However, insoluble soy or of *L. campestris* products can also be used in the present invention to replace animal products. Common animal derived products which can be substituted by soy or of *L. campestris* products include beef heart infusion (BHI), animal derived peptone products, such as Bacto-peptone, hydrolyzed caseins, and dairy by-products such as animal milk.

Preferably media containing soy-based or of *L. campestris* based products for the growth of *Clostridium botulinum* are similar to commonly used growth media containing animal derived products except that substantially all animal-derived products are replaced with vegetable-derived products. For example, soy based fermentation media can comprise a soy based product, a source of carbon such as glucose, salts such as NaCl and KCl, phosphate-containing ingredients such as $Na_2HPO_4$, $KH_2PO_4$, divalent cations such as iron and magnesium, iron powder, and amino acids such as L-cysteine and L-tyrosine. Media used to grow cultures of *Clostridium botulinum* for inoculation (i.e. the seed or first medium) of the fermentation (second) media preferably contain at least a soy based product, a source of salt such as NaCl, and a carbon source such as glucose.

The present invention provides a method for the growth of *Clostridium botulinum* that maximizes the production of a botulinum toxin using media that are substantially free of animal-derived products. Growth of *Clostridium botulinum* for production of botulinum toxin can take place by fermentation in media containing soy by-products that replace ingredients derived from animal by-products. The inoculant for the fermentation medium can be derived from a smaller scaled growth medium (a seed medium). Depending on the size and volume of the fermentation step, the number of successive growths in seed media to increase the biomass of the culture can vary. To grow a suitable amount of *Clostridium botulinum* for inoculating the fermentation medium, one step or multiple steps involving growth in a seed medium can be performed. For a method of growing *Clostridium botulinum* that is free of animal derived products, it is preferable that growth of *Clostridium botulinum* originates from a culture stored in non animal derived media. The stored culture, preferably lyophilized, is produced by growth in media containing proteins derived from soy and lacking animal by-products. Growth of *Clostridium botulinum* in a fermentation medium can take place by inoculation directly from a stored, lyophilized culture.

In a preferred embodiment of the present invention, growth of *Clostridium botulinum* proceeds in two phases-seed growth and fermentation. Both of these phases are carried out in anaerobic environments. The seed growth phase is generally used to "scale-up" the quantity of the microorganism from a stored culture. The purpose of the seed growth phase) is to increase the quantity of the microorganism available for fermentation. In addition, the seed growth phase allows relatively dormant microbes in stored cultures to rejuvenate and grow into actively growing cultures. Furthermore, the volume and quantity of viable microorganisms used to inoculate the fermentation culture can be controlled more accurately from an actively growing culture than from a stored culture. Thus, growth of a seed culture for inoculation of the fermentation medium is preferred. In addition, any number of consecutive steps involving growth in seed media to scale-up the quantity of *Clostridium botulinum* for inoculation of the fermentation medium can be used. It is noted that growth of *Clostridium*

*botulinum* in the fermentation phase can proceed directly from the stored culture by direct inoculation.

In the fermentation phase, a portion of a seed medium or all of a seed medium containing *Clostridium botulinum* from the seed growth is used to inoculate a fermentation medium. Preferably, approximately 2-4% of a seed medium having *Clostridium botulinum* from the seed growth phase is used to inoculate the fermentation medium. Fermentation is used to produce the maximum amount of microbe in a large-scale anaerobic environment (Ljungdahl et al., *Manual of industrial microbiology and biotechnology* (1986), edited by Demain et al, American Society for Microbiology, Washington, D.C. page 84).

A botulinum toxin can be isolated and purified using methods of protein purification well known to those of ordinary skill in the protein purification art. See e.g. Coligan et al. *Current Protocols in Protein Science*, Wiley & Sons; Ozutsumi et al. Appl. Environ. Microbiol. 49; 939-943:1985.

For production of botulinum toxin, cultures of *Clostridium botulinum* can be grown in a seed medium for inoculation of the fermentation medium. The number of successive steps involving growth in a seed medium can vary depending on the scale of the production of botulinum toxin in the fermentation phase. However, as previously discussed, growth in the fermentation phase may proceed directly from inoculation from a stored culture. Animal-based seed media generally are comprised of BHI, bacto-peptone, NaCl, and glucose for growth of *Clostridium botulinum*. As previously discussed, alternative seed media may be prepared in accordance with the present invention in which animal-based components are substituted with non-animal-based components. For example but without limitation, soy-based products can substitute for BHI and bacto-peptone in the seed medium for growth of *Clostridium botulinum* and production of botulinum toxin. Preferably, the soy-based product is soluble in water and comprises hydrolyzed soy, although cultures of *Clostridium botulinum* can grow in media containing insoluble soy. However, levels of growth and subsequent toxin production are greater in media derived from soluble soy products.

Any source of soy-based products may be used in accordance with the present invention. Preferably, the soy is hydrolyzed soy and the hydrolyzation has been carried out using non-animal enzymes. Sources of hydrolyzed soy are available from a variety of commercial vendors. These include but are not limited to Hy-Soy (Quest International), Soy peptone (Gibco) Bac-soytone (Difco), AMISOY (Quest), NZ soy (Quest), NZ soy BL4, NZ soy BL7, SE50M (DMV International Nutritionals, Fraser, N.Y.), and SE50MK (DMV). Most preferably, the source of hydrolyzed soy is Hy-Soy or SE50MK. Other potential sources of hydrolyzed soy are known.

Concentrations of Hy-Soy in the seed medium in accordance with the present invention range between 25-200 g/L. Preferably, the concentration of Hy-Soy in the seed medium ranges between 50-150 g/L. Most preferably the concentration of Hy-Soy in the seed medium is approximately 100 g/L. In addition, the concentration of NaCl ranges between 0.1-2.0 g/L. Preferably the concentration of NaCl ranges between 0.2-1.0 g/L. Most preferably, the concentration of NaCl in the seed medium is approximately 0.5 g/L. The concentration of glucose ranges between 0.1 g/L and 5.0 g/L. Preferably, the concentration of glucose ranges between 0.5-2.0 g/L. Most preferably, the concentration of glucose in the seed medium is approximately 1.0 g/L. It is also preferred but not necessary for the present invention that the glucose is sterilized by autoclaving together with the other components of the seed medium. The pH level of the seed medium prior to growth can be 7.5-8.5. For example, the pH of the seed medium prior to growth of *Clostridium botulinum* can be approximately 8.1.

Growth of *Clostridium botulinum* in the seed medium can proceed in one or more stages. Preferably, growth in the seed medium proceeds in two stages. In stage one, a culture of *Clostridium botulinum* is suspended in a quantity of seed medium and incubated at 34±1° C. for 24-48 hours in an anaerobic environment. Preferably, growth in stage one proceeds for approximately 48 hours. In stage two, a portion or all of the stage one medium containing *Clostridium botulinum* is used to inoculate a stage two seed medium for further growth. After inoculation, the stage two medium is incubated at 34±1° C. for approximately 1-4 days also in an anaerobic environment. Preferably, growth in the stage two seed medium proceeds for approximately 3 days. It is also preferable that growth in seed media in any stage does not result in cell lysis before inoculation of fermentation media with the final growth in seed medium.

Standard fermentation media containing animal by-products for the growth of *Clostridium botulinum* can be based on a recipe of Mueller and Miller (MM; J. Bacteriol. 67:271, 1954). The ingredients in MM media containing animal by-products include BHI and NZ-CaseTT. NZ-CaseTT is a commercially available source of peptides and amino acids which are derived from the enzymatic digestion of caseins, a group of proteins found in animal milk. The present invention demonstrates that non-animal based products may be substituted for BHI and NZ-CaseTT in fermentation media. For example but without limitation, soy-based products can replace the animal-based components of MM media used for fermentation of *Clostridium botulinum*. Preferably, the soy-based products are water-soluble and derived from hydrolyzed soy, although as previously discussed, insoluble soy products can also be used to practice the present invention.

Any source of soy-based products may be used in accordance with the present invention. Preferably, the hydrolyzed soy is obtained from Quest International (Sheffield) under the tradename, Hy-Soy or from DMV International Nutritionals (Fraser, N.Y.) under the tradename, SE50MK. Soluble soy products can be also obtained from a variety of sources including but not limited to Soy peptone (Gibco) Bac-soytone (Difco), AMISOY (Quest), NZ soy (Quest), NZ soy BL4, NZ soy BL7, and SE50MK (DMV International Nutritionals, Fraser, N.Y.).

In another preferred embodiment of the present invention, the medium used for fermentation of *Clostridium botulinum* is free of animal by-products and comprises hydrolyzed soy, glucose, NaCl, $Na_2HPO_4$, $MgSO_4 7H_2O$, $KH_2PO_4$, L-cysteine, L-tyrosine, and powdered iron. As disclosed for the seed medium, hydrolyzed soy can replace animal by-products in fermentation medium. These animal by-products include BHI and NZ-Case TT (enzymatically digested casein).

The concentration of Hy-Soy in the fermentation medium for production of botulinum toxin preferably ranges between approximately 10-100 g/L. Preferably, the concentration of Hy-Soy ranges between approximately 20-60 g/L. Most preferably, the concentration of Hy-Soy in the fermentation medium is approximately 35 g/L. For maximal production of botulinum toxin, particularly preferred concentrations of components in the fermentation medium are approximately 7.5 g/L, glucose; 5.0 g/L NaCl; 0.5 g/L $Na_2HPO_4$; 175 mg/L $KH_2PO_4$; 50 mg/L $MgSO_4 7H_2O$; 125 mg/L L-cysteine; and 125 mg/L L-tyrosine. The amount of powdered iron used can range from 50 mg/L to 2000 mg/L. Preferably, the amount of powdered iron ranges between approximately 100 mg/L and 1000 mg/L. Most preferably, the amount of powdered iron used in fermentation media ranges between approximately 200 mg/L and 600 mg/L.

For optimal levels of toxin production, the initial pH (before autoclaving) of the soy-based fermentation media ranges preferably between approximately 5.0 to 7.1. We found that pH control improves botulinum toxin recovery. Preferably the initial pH of the fermentation medium is about pH 7. As explained in Example 7, we have found that a high yield of stable botulinum toxin can be obtained if the pH is thereafter reduced to and maintained between pH 5-5.5. As described for the seed medium, the components of the fermentation medium, including glucose and iron, are preferably autoclaved together for sterilization.

Preferably, a portion of the second stage seed medium used for growth of *Clostridium botulinum* is used to inoculate the fermentation medium. Fermentation occurs in an anaerobic chamber at approximately 34.±1° C. for approximately 7 to 9 days. Bacterial growth can be monitored by measuring the optical density (O.D.) of the medium. Fermentation preferably is stopped after cell lysis has proceeded for at least 48 hours as determined by growth measurement (optical density). As cells lyse, the O.D. of the medium decreases.

In a preferred embodiment of the present invention, cultures of *Clostridium botulinum* used for long-term storage of *Clostridium botulinum* and inoculation of the seed medium are grown and lyophilized in soy-milk prior to storage at 4° C. Cultures of *Clostridium botulinum* in animal milk lyophilized for storage can also be used for the production of botulinum Toxin. However, to maintain media that are substantially free of animal by-products throughout the production of botulinum toxin, it is preferred that the initial culture of *Clostridium botulinum* be preserved in soy milk and not animal milk.

EXAMPLES

The following examples set forth specific methods encompassed by the present invention and are not intended to limit the scope of the invention. Unless explained otherwise in these Examples "toxin" or "botulinum toxin" means a botulinum toxin type A complex with a molecular weight of about 900 kDa. Our invention is not limited to systems and method for purifying a botulinum toxin type A complex with a molecular weight of about 900 kDa, having ready applicability to the purification of 150 kDa, 300 kDa, 500 kDa and well as other molecular weight toxins, complexes and botulinum toxin serotypes.

Example 1

Preparation of an Animal Product Free Seed Medium for *Clostridium Botulinum*

A control seed medium can be prepared using the following ingredients for each one 1 liter of medium: NaCl (5 g), Bacto-peptone (10 g), glucose (10 g), BHI (to 1 liter), pH 8.1 (adjusted with 5 N NaOH).

A test (animal product free) seed medium can be prepared using the following ingredients for each one 1 liter of medium: NaCl (5 g), Soy-peptone (10 g), glucose (10 g), Hy-Soy (35 g/liter, to make up 1 liter of media fluid), pH 8.1 (adjusted with 5 N NaOH).

Example 2

Culturing *Clostridium Botulinum* in an Animal Product Free Seed Medium

A lyophilized culture of the *Clostridium botulinum* can be suspended in 1 ml of each of the control and test seed medium of Example 1, divided (each seed media) into two tubes of which each can contain 10 ml of the respective seed media, and then incubated at 34° C. for about 24-48 hours. One ml of culture can be then used to inoculate a 125 ml DeLong Bellco Culture Flask containing 40 ml of (the respective) seed media. The inoculated culture can be incubated at 33° C.±1° C. for 24 hours in a Coy Anaerobic Chamber (Coy Laboratory Products Inc., Grass Lake, Mich.).

Example 3

Preparation of an Animal Product Free Fermentation Media for *Clostridium Botulinum*

A basal fermentation medium can be prepared using the following ingredients for each two liters of medium: glucose (15 g), NaCl (10 g), $NaH_2PO_4$ (1 g), $KH_2PO_4$ (0.350 g), $MgSO_4 7H_2O$ (0.1 g), cysteine-HC (0.250 g), tyrosine-HCl (0.250 g), powdered iron (1 g), $ZnCl_2$ (0.250 g), and $MnCl_2$ (0.4 g).

A control fermentation medium can be prepared using the following ingredients for each two liters of medium prepared: BHI (500 ml; this corresponds to about 45.5 grams of dry weight beef heart infusion), NZ-CaseTT (30 g), and basal medium (to 2 liters), pH 6.8.

The basal fermentation medium can be prepared first and adjusted to pH 6.8. The beef heart infusion (BHI) BHI can then be prepared and it's pH adjusted to 0.8 with 5 N NaOH. The BHI can then be added to the basal medium. Next the NZ-CaseTT can be prepared. The NZ-Case TT is then added to the to basal medium to which the beef heart infusion has already been added, and dissolved by addition of HCl. The pH can then be adjusted to 6.8 with 5 N NaOH. This medium can then be separated into 8 ml portions into each of sixteen 100 mm test tubes, following by autoclaving for 25 minutes at 120° C.

A test fermentation medium (animal product free) can be prepared by substituting a test nitrogen source for the BHI present in the control fermentation medium. Suitable test fermentation medium nitrogen sources include: Hy-Soy (Quest), AMI-Soy (Quest), NZ-Soy (Quest), NZ-Soy BL4 (Quest), NZ-Soy BL7 (Quest), Sheftone D (Sheffield), SE50M (DMV), SE50 (DMV), SE %) MK (DMV), Soy Peptone (Gibco), Bacto-Soyton (Difco), Nutrisoy 2207 (ADM), Bakes Nutrisoy (ADM) Nutrisoy flour, Soybean meal, Bacto-Yeast Extract (Difco) Yeast Extract (Gibco), Hy-Yest 412 (Quest), Hy-Yest 441 (Quest), Hy-Yest 444 (Quest), Hy-Yest (455 (Quest) Bacto-Malt Extract (Difco), Corn Steep, and Proflo (Traders).

The test fermentation medium can be prepared as set forth above for a control fermentation medium except that BHI is excluded and the relevant nitrogen source can be first adjusted to pH 6.8 with 3 N HCl or with 5 N NaOH. The media can be allocated to in 8 ml portions to sixteen 100 mm test tubes, followed by autoclaving for 20-30 minutes at 120° C.

Example 4

Growth of *Clostridium Botulinum* in an Animal Product Free Fermentation Medium

A 40 μl portion of the test seed medium culture (animal product free) can be used to inoculate each 8 ml control or test fermentation medium aliquot in an 8 ml 16×100 mm test tube. The cultures can then be incubated at 33±1° C. for 24 hours. Tubes can then be incubated in an anaerobic chamber to allow for growth of the bacterium. Each medium assay can be performed in triplicate (i.e. can involve three independent inoculations of the same medium), and can also include a non-inoculated control, which can be used as the blank for the spectrophotometer). Growth (as determined by optical density, OD) can be measured every 24 hours with a Turner Spectrophotometer (Model 330) at 660 nm. Cultivation should be stopped after cell lysis has lasted for about 48 hours and botulinum toxin production can then be measured.

Additional experiments can be carried out with a Hy-Soy fermentation medium containing the following ingredients for each 500 ml of the medium: Hy-Soy (17.5 g), glucose (3.75 g); NaCl (2.5 g); $Na_2HPO_4$ (0.25 g), $MgSO_4 7H_2O$ (0.025 g), $KH_2PO_4$ (0.0875 g), L-cysteine (0.0625 g), L-tyrosine (0.0625 g), powdered iron (0.25 g), pH 6.8

Example 5

Determination of Botulinum Toxin Production by *Clostridium Botulinum* Grown in an Animal Product Free Fermentation Medium The cultured cells of Example 4 can be centrifuged, and the pH of the supernatant then determined. The levels of botulinum toxin in a given sample can be measured by adding a standard antitoxin and measuring the elapsed time before flocculation. Both Kf (the time required for flocculation to occur, in minutes) and Lf (the limit of flocculation; equivalent to 1 international unit of standard antitoxin, as established by flocculation) can be determined. 4 ml of fermentation broth can be taken from each fermentation tube for a given culture, and can be combined together so that 12 ml total can be mixed in a 15 ml centrifuge tube. The tubes can be centrifuged at 5000 rpm (3400 g) for 30 min at 4° C. 1 ml aliquots of supernatant can be added to tubes containing 0.1-0.6 ml of standard botulinum toxin antiserum, and the tubes can be carefully shaken to mix their contents. The tubes can then be placed in a water bath at 45±1° C. and the initial time can be recorded. The tubes can be checked frequently, and the time at which flocculation began can be recorded as Kf. The concentration of toxin in the tube in which flocculation can be first initiated can be designated LfFF. The concentration of toxin in the tube in which flocculation can be initiated second can be designated LfF.

Parallel fermentation, growth and toxin production assays can be carried out for both of: (a) the control seed medium (used to inoculate the control fermentation medium) and the control fermentation medium, and; (2) the (animal product free) test seed medium (used to inoculate the test fermentation medium) and the (animal product free) test fermentation medium. Significantly, it can be determined that the fermentation of *Clostridium botulinum* in media free of animal products and inoculated from cultures also free of animal products (with soy-base products replacing the animal products) can result in an $Lf_{toxin}$ of approximately 50 or more. Minimally, $Lf_{toxin}$ equals approximately 10. Preferably the $Lf_{toxin}$ at least 20. Most preferably the $Lf_{toxin}$ greater than 50.

Additionally, it can be determined that various soy products support *Clostridium botulinum* growth in fermentation media lacking BHI. Thus soluble soy preparations can replace BHI for growth of *Clostridium botulinum*. The best concentration can be 12.5 or 25 g/L. Hy-Soy (Sheffield) can give the highest growth. Insoluble soy preparations can be less effective.

Furthermore, results can be obtained to show that Quest Hy-Soy, DMV SE50MK, and Quest NZ-Soy can be effective soy products in terms of their ability to replace BHI for *Clostridium botulinum* growth. The results can reveal that the soy products (such as Quest Hy-Soy, DMV SE50MK, and Quest NZ-Soy) that may be optimal for growth can also be effective at replacing BHI for toxin production. The best soy product for toxin production can be Quest Hy-Soy at 22.75 g/l. Higher concentrations of this product may produce better growth but not improve toxin production. Similar results can, it is proposed, be obtained with SE50MK, for which a higher concentration may generate increased growth, but not increase toxin production. NZ-Soy, on the other hand, may give higher growth and higher toxin production at its higher concentration.

Finally, it can be determined that soy products can effectively replace BHI as well as the NZ-CaseTT. Removal of NZ-CaseTT from soy-based media can reduce growth of about 2-4 fold. The best soy product for growth both in the presence and the absence of NZ-CaseTT can be SE50MK. HY-Soy can replace both BHI and NZ-CaseTT for toxin production. However, a longer fermentation cycle of 1 or 2 days may be necessary. HY-Soy could replace both BHI and NZ-CaseTT in media for toxin production. However, it can be determined that yeast extracts can be inhibitory to toxin production.

It can be determined that HY-Soy at 22.75 WI may completely replace both BHI and HY-CaseTT for toxin production. Unlike the effect on growth where 56.88 WI HY-Soy can be best, 34.13 WI HY-Soy can be best for the toxin production phase.

Thus, it has surprisingly been determined if Hy-Soy or [Hy-Soy+Hy-Yest] can replace BHI and Bacto-peptone in media for seed growth of *Clostridium botulinum*. In addition, experiments can be designed to determine the optimum concentrations of components in seed media to produce the maximum levels of botulinum toxin production by the *Clostridium botulinum*. Toxin production by *Clostridium botulinum* grown in seed medium and fermentation medium that is free of BHI and NZ-CaseTT can reach or exceed levels attained in media containing BHI and NZ-CaseTT.

It can be determined that the optimum concentrations of Hy-Soy or [Hy-Soy+Hy-Yest] for growth in the seed medium. Experiments can confirm that Hy-Soy can replace BHI and Bacto-peptone as the nitrogen source in seed medium for growth of *Clostridium botulinum* and for production of botulinum toxin in the subsequent fermentation phase. Also, Hy-Soy as nitrogen source in the seed medium, as compared to Hy-Soy plus Hy-Yest, can produce higher levels of botulinum toxin in the subsequent fermentation step. The concentrations of Hy-Soy in seed medium that produce the best levels of toxin range from approximately 62.5 g/L to 100 g/L.

Additional experiments can be designed to determine the optimum concentrations of Hy-Soy in the seed medium for the maximum production of botulinum toxin by *Clostridium botulinum* by fermentation. Thus, 30 g, 50 g, 75 g and 100 g of Hy-Soy in the seed medium can all resulted in production of botulinum toxin by fermentation of *Clostridium botulinum* and this is comparable or exceeds levels of botulinum toxin made in seed medium containing BHI and Bacto-peptone as a nitrogen source.

It can be found that a concentration of 100 g/L Hy-Soy in the seed medium resulted in the highest levels of toxin production in the subsequent fermentation step. In addition, the data indicate that seed step-1 of Hy-Soy seed medium produced greater growth after 48 hours than after 24 hours.

Example 6

Non-APF Process for Obtaining a Botulinum Toxin

A Clostridial toxin was obtained by fermentation of a *Clostridium botulinum* bacterium. Thus, a modified Schantz (non-APF) process was carried out to obtain highly potent and highly purified *Clostridium botulinum* toxin (i.e. bulk toxin) as follows. A modified Schantz (non-APF) process can provide a high yield of botulinum toxin. Both Schantz and modified Schantz processes use casein in all the fermentation media.

Stock Culture Preparation

Figure 1:
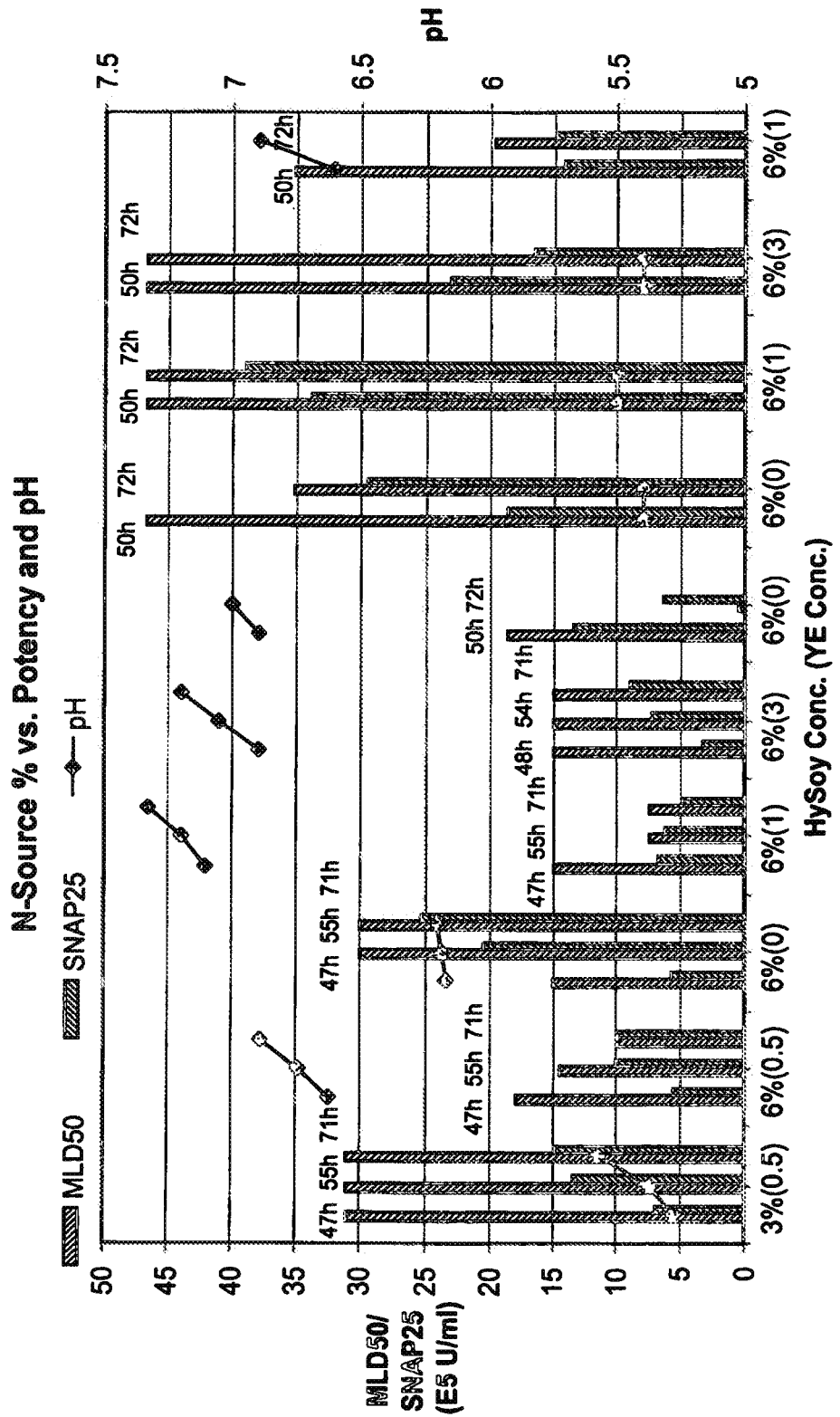

Various Clostridial bacteria are available from the American Type Culture Collection (ATCC), Manassas, Va. Alternately, a *Clostridium botulinum* cell bank vial can be prepared by isolating *Clostridium botulinum* from various sources, including soil or by deep sampling (at anaerobic or at quasi-anaerobic locations) of putrefying animal carcasses. Commonly, *Clostridium botulinum* can be obtained from a sample of a physiological fluid (i.e. a wound swap from a patient with wound botulism) of a patient diagnosed with botulism. The top half of FIG. 1 summarizes the non-APF process used for preparation of a cell bank vial, and for the culture and fermentation of a botulinum toxin.

The *Clostridium botulinum* obtained from a natural or patient source is cultured on blood agar plates, followed by inoculation of high growth colonies into a cell bank vial medium. The cell bank vial medium used for *Clostridium botulinum* was a cooked meat medium which contains chopped fresh beef. Actively growing cultures were mixed with glycerol to prepare a cell bank vial (i.e. a stock culture) of the *Clostridium botulinum* bacterium which was frozen for later use.

Seed Cultivations

A *Clostridium botulinum* cell bank vial was thawed at room temperature, followed by four cultivation steps. (1) To select colonies with a suitable morphology, aliquots from the thawed cell bank vial were cultivated by streaking the bacterium on pre-reduced Columbia blood agar plates and anaerobically incubating for 30-48 hours at 34° C.±1°. (2) Selected colonies were then inoculated into test tubes containing a casein growth medium for 6-12 hours at 34° C. The contents of the tube with the most rapid growth and highest density (growth selection step) were then further cultivated through two step-up anaerobic incubations: (3) a first 12-30 hour incubation at 34° C. in a one liter seed cultivation bottle, followed by (4) a second cultivation in a 25 liter seed fermenter containing a casein growth medium for 6-16 hours at 35° C. These two step-up cultivations were carried out in a nutritive media containing 2% casein hydrolysate (a casein [milk protein] digest), 1% yeast extract and 1% glucose (dextrose) in water at pH 7.3.

Fermentation

The step-up cultivations were followed by a further incubation for 60-96 hours at 35° C. in a commercial scale (i.e. 115 liter) fermenter in a casein containing medium under a controlled anaerobic atmosphere. Growth of the bacterium is usually complete after 24 to 36 hours, and during the 60-96 hour fermentation most of the cells undergo lysis and release botulinum toxin. Control of the fermentation medium pH is not required in a Schantz or modified Schantz process. It is believed that toxin is liberated by cell lysis and activated by proteases present in the culture broth. Optionally, a filtration of this culture medium using a single layer depth filter to remove gross impurities (i.e. whole and ruptured cells) can be prepared to obtain a clear solution referred to a clarified culture.

Harvest

Harvest of toxin can be accomplished by lowering the pH to 3.5 with sulfuric acid to precipitate the raw toxin at 20° C. The raw toxin was then concentrated by ultramicrofiltration followed by diafiltration.

Purification

The harvested crude toxin was then transferred to a digestion vessel and stabilized by addition of the protease inhibitor benzamidine hydrochloride. DNase and RNase were added to digest nucleic acids. The toxin containing material was subjected to UF/DF and three precipitation steps (cold ethanol, hydrochloric acid and ammonia sulfate precipitations). The purified botulinum neurotoxin complex (bulk toxin) was stored as a suspension in a sodium phosphate/ammonium sulphate buffer at 2-8 degrees C.

The resulting bulk toxin was a high quality crystalline 900 kD botulinum toxin type A complex made from the Hall A strain of *Clostridium botulinum* with a specific potency of $\geq 3 \times 10^7$ U/mg, an $A_{260}/A_{278}$ of less than 0.60 and a distinct pattern of banding on gel electrophoresis, and suitable for use for the compounding of a botulinum toxin pharmaceutical composition.

Compounding can encompass a many fold dilution of the bulk toxin, mixing with one or more excipients (such as albumin and sodium chloride) to thereby form a toxin composition, and preparation of a storage and shipment stable form of the toxin composition, as by lyophilizing, freeze drying or vacuum drying the composition.

The purified botulinum toxin complex obtained from a Schantz or modified Schantz process can be eluted from an ion exchange column in a pH 7-8 buffer to disassociate the non toxin complex proteins from the botulinum toxin molecule, thereby providing (depending upon the type of *Clostridium botulinum* bacterium fermented) pure botulinum toxin type A with an approximately 150 kD molecular weight, and a specific potency of $1-2 \times 10^8$ $LD_{50}$ U/mg or greater; or purified botulinum toxin type B with an approximately 156 kD molecular weight and a specific potency of $1-2 \times 10^8$ $LD_{50}$ U/mg or greater, or purified botulinum toxin type F with an approximately 155 kD molecular weight and a specific potency of $1-2 \times 10^7$ $LD_{50}$ U/mg or greater.

As set forth supra, in one aspect our invention eliminates the harvest purification steps set forth in this Example 6 carried out upon clarified culture, including elimination of use of the animal derived products, such as RNase and DNase.

Example 7

APF Media and Process for Obtaining a Botulinum Toxin

This Example 7 sets forth an APF process carried out to obtain highly potent and highly purified *Clostridium botulinum* toxin type A (i.e. bulk toxin). The process can be used with other botulinum toxin serotypes.

Stock Culture Preparation

As set forth in Example 6, Clostridial botulinum can be obtained from the ATCC, from various sources in nature or from a botulism patient. The bottom half of FIG. 1 summarizes the APF process used for preparation of a cell bank vial, and for the culture and fermentation of a botulinum toxin. APF cell bank vials were prepared by culturing *Clostridium botulinum* on plant agar plates. The plant agar plates were made by mixing the soy derivative HySoy (Quest) with a yeast extract and glucose in a 3:1:1 (weight percent) ratio with agar and allowing setting. Other commercially available APF agar plates or dehydrated powder for making the plates were also found to be suitable. Selected high growth colonies were then inoculated into an APF cell bank vial medium. The APF cell bank vial medium used comprised hydrolyzed soy protein, yeast extract (no animal product was used in either the cultivation of the yeast or in the process for preparation of the yeast extract made therefrom) and glucose in the same 3:1:1 ratio. Other nutrient ratios (i.e. 6:1:1, 6:0:1 and 6:3:1 were also found to be suitable). The hydrolyzed soy (HySoy) and yeast extract (HyYest) concentrates used were obtained from Quest International. The *Clostridium botulinum* culture in the APF medium was combined with glycerol, aliquoted to cryovials and frozen for later use. The APF media developed can be used to store the Clostridial botulinum bacteria for a period of one year or longer without loss of viability. These frozen culture and glycerol mixtures in cryovials are the APF cell bank vials.

Seed Cultivations

An APF cell bank vial was thawed at room temperature, followed by a single cultivation step: a one liter seed culture bottle was then inoculated directly (i.e. without an intervening blood agar culture or tube growth steps) with the APF cell bank vial contents using the same APF medium (the APF cell bank vial [storage] medium can be different from the APF fermentation [growth] medium) and maintained at 35° C. for 15 to 24 hours, with an initial medium pH of 7.0 in an anaerobic (nitrogen) atmosphere.

Fermentation

Next the seed bottle culture was transferred to a commercial scale 10 liter production fermenter containing the APF medium (hydrolyzed soy protein, yeast extract and 1% glucose) maintained at 35° C. for 52-72 hours, with an initial medium pH of 7.0, in an anaerobic (nitrogen) atmosphere. Approximately 15 hours after commencement of the fermentation (the culture pH has naturally decreased to below 6.0), a pH control program at range of pH 5.0-5.5 was initiated by adding HCl to the culture. It was found that it was necessary to control the pH of the APF fermentation medium within the narrow range in order to obtain an acceptable yield of active botulinum toxin. Thus, it was found that this pH control to between pH 5.0-5.5 substantially prevented degradation and loss of potency of the botulinum toxin. It is believed that during the fermentation most of the cells undergo lysis and release botulinum toxin and that toxin liberated by cell lysis is activated by proteases present in the culture broth. Filtration of this culture medium using a single layer depth filter removes gross impurities (i.e. whole and ruptured cells) and results in a clear solution referred to a clarified culture.

Harvest

Harvest of botulinum toxin can then proceed as in Example 6 (i.e. sulfuric acid precipitation, followed by concentrated by microfiltration followed by diafiltration).

Purification

Purification of the toxin can then proceed as set forth in Example 6: i.e. addition of benzamidine hydrochloride, and DNase and RNase, sulfuric acid precipitation, cold ethanol precipitation, phosphate buffer extraction, hydrochloric acid precipitation, phosphate buffer extraction and bulk toxin storage.

As an alternative to the Example 6 harvest and purification process, a column chromatography process of the present invention can be carried out.

The resulting bulk toxin is a high quality crystalline 900 kD botulinum toxin type A complex made from the Hall A strain of *Clostridium botulinum* with a specific potency of $\geq 3 \times 10^7$ U/mg, an $A_{260}/A_{278}$ of less than 0.60 and a distinct pattern of banding on gel electrophoresis, and suitable for use for the compounding of a botulinum toxin pharmaceutical composition. Thus, this APF process for a botulinum toxin can generate high quality toxin.

The purified botulinum toxin complex obtained from an APF process can be passed through and eluted from an ion exchange column in a pH 7-8 buffer to disassociate the non toxin complex proteins from the botulinum toxin molecule, thereby providing (depending upon the serotype of *Clostridium botulinum* bacterium fermented) botulinum toxin with an approximately 150 kD molecular weight, and a specific potency of $1\text{-}2\times10^8$ $LD_{50}$ U/mg or greater; or purified botulinum toxin type B with an approximately 156 kD molecular weight and a specific potency of $1\text{-}2\times10^8$ $LD_{50}$ U/mg or greater, or purified botulinum toxin type F with an approximately 155 kD molecular weight and a specific potency of $1\text{-}2\times10^7$ $LD_{50}$ U/mg or greater. For example, by use of our APF medium we were able to obtain a botulinum toxin type A complex with a specific potency of $1.02\times10^8$ $LD_{50}$ U/mg of the botulinum toxin.

In this Example 7 APF media with either 1% by wt or 2% by wt glucose were used (note that 1% glucose means 1 g of glucose per 100 ml of the culture medium and 2% glucose means 2 g of glucose were present for each 100 ml of the culture medium) and it was determined that maximal bacterium growth (as determined by peak optical density [optical density was measured at 600 nm] of the culture) occurred after about 20 hours of fermentation in the 1% glucose APF medium vs after about 40 hours of fermentation in the 2% glucose APF medium, but that the peak optical densities did not differ significantly as the glucose content of the media was so varied. It was believed that cell autolysis and toxin release resulted in a maximal amount of active botulinum toxin in the 1% glucose APF media (as determined by a SNAP-25 assay for active toxin) after about 55 hours of fermentation, but that with the 2% glucose APF media the amount of active botulinum toxin present in the medium at a later time (as determined by a SNAP-25 assay for active toxin) and was still increasing after 65 hours of fermentation. Thus, a more rapid release of botulinum toxin occurred with use of the lower (1%) glucose APF medium amount present, indicating that a more efficient toxin production process (i.e. more amount of toxin obtained per unit of time) can be carried out with use of the lower (1%) glucose APF medium.

As shown by FIG. 1, it was also determined that optimal parameters for production of botulinum toxin in an APF medium were the combination of the following parameters: (1) about 6% by weight of a hydrolyzed soy concentration ("HySoy Conc." in FIG. 1) in the APF fermentation medium. 6% soy means 6 g of the soy protein per 100 ml of the culture medium; (2) 0% to 3% yeast extract concentrate ("YE Conc." In FIG. 1) in the APF fermentation medium; (3) 50-72 hours of fermentation at a temperature of 33-35° C. under anaerobic (nitrogen atmosphere) conditions; (4) pH of the fermentation medium maintained between about pH 5.0 to 5.5 throughout the fermentation period after the initial cell growth, and (5) 1 wt % glucose in the APF fermentation medium.

Thus, as shown by FIG. 1 as more protein is present in the APF medium (as the total amount of HySoy and YE) the pH of the medium tends to increase with resulting lower toxin stability and that when the pH was lowered with the same total protein nutrient content in the medium, toxin production yield increased dramatically. In the non-APF process the total protein content is lower so that pH does not tend to rise and therefore there is no elevated pH to have a deleterious effect on toxin production. FIG. 1 shows that there was consistently more activity (as determined by the MLD50 and SNAP-25 assays) when the pH of the medium was controlled to within a narrow range of about 5.3 to 5.5. FIG. 1 also shows that the highest toxin yield (as determined by the SNAP 25 assay) was obtained with a medium which comprised 6% hydrolyzed soy and 1% yeast extract. FIG. 8 shows that when the yeast and glucose nutrients were both at 1%, that cell lysis between 68-100% and potency as high as about $38 \times 10^5$ units/mL of toxin was obtained, as soy protein was varied from 1 to 6% weight.

The SNAP-25 assay used was an ELISA based method to measure SNAP-25 proteolytic activity of the botulinum toxin. SNAP-25 is an abbreviation for synaptosome associated protein of 25 kDa molecular weight. SNAP-25 is a 206 amino acid plasma membrane protein involved in neuronal exocytosis. The assay is based on the method disclosed in Ekong T., et al., *Recombinant SNAP-25 is an effective substrate for Clostridium botulinum type A toxin endopeptidase activity in vitro*, Microbiology (1997), vol 143, pages 3337-3347. The assay uses a truncated SNAP-25 protein (the 206 amino acid residue peptide) bound to polystyrene 96 well microtiter plates and a monoclonal antibody that recognizes the cleaved product (a 197 amino acid residue peptide) which is made by enzymatic hydrolysis between amino acids 197 and 198 of the SNAP-25 by reduced botulinum toxin type A. The monoclonal antibody bound to the cleaved product is then detected with a secondary antibody (goat anti-mouse IgG conjugated to horseradish peroxidase [HRP)], which produces a color change in the presence of a chromogenic substrate (TMB).

The MLD50 (mouse 50% lethal dose) assay is a method for measuring the potency of a botulinum toxin by intraperitoneal injection of the botulinum toxin into female mice (about four weeks old) weighing 17-22 grams each at the start of the assay. Each mouse is held in a supine position with its head tilted down and is injected intraperitoneally into the lower right abdomen at an angle of about 30 degrees using a 25 to 27 gauge ⅜" to ⅝" needle with one of several serial dilutions of the botulinum toxin in saline. The death rates over the ensuing 72 hours for each dilution are recorded. The dilutions are prepared so that the most concentrated dilution produces a death rate of at least 80% of the mice injected, and the least concentration dilution produces a death rate no greater than 20% of the mice injected. There must be a minimum of four dilutions that fall within the monotone decreasing range of the death rates. The monotone decreasing range commences with a death rate of no less than 80%. Within the four or more monotone decreasing rates, the two largest and the two smallest rates must be decreasing (i.e. not equivalent). The dilution at which 50% of the mice die within the three day post injection observation period is defined as a dilution which comprises one unit (1 U) of the botulinum toxin.

Significantly, the APF process of this Example 7 differs from the Example 6 non-APF process, by at least: (1) replacing the cell bank vial cooked meat medium with an APF medium; (2) eliminating the blood agar colony selection step; (3) eliminating the subsequent casein medium based tube growth step, and; (4) replacing the non-APF fermentation media with APF media throughout.

Figure 2:
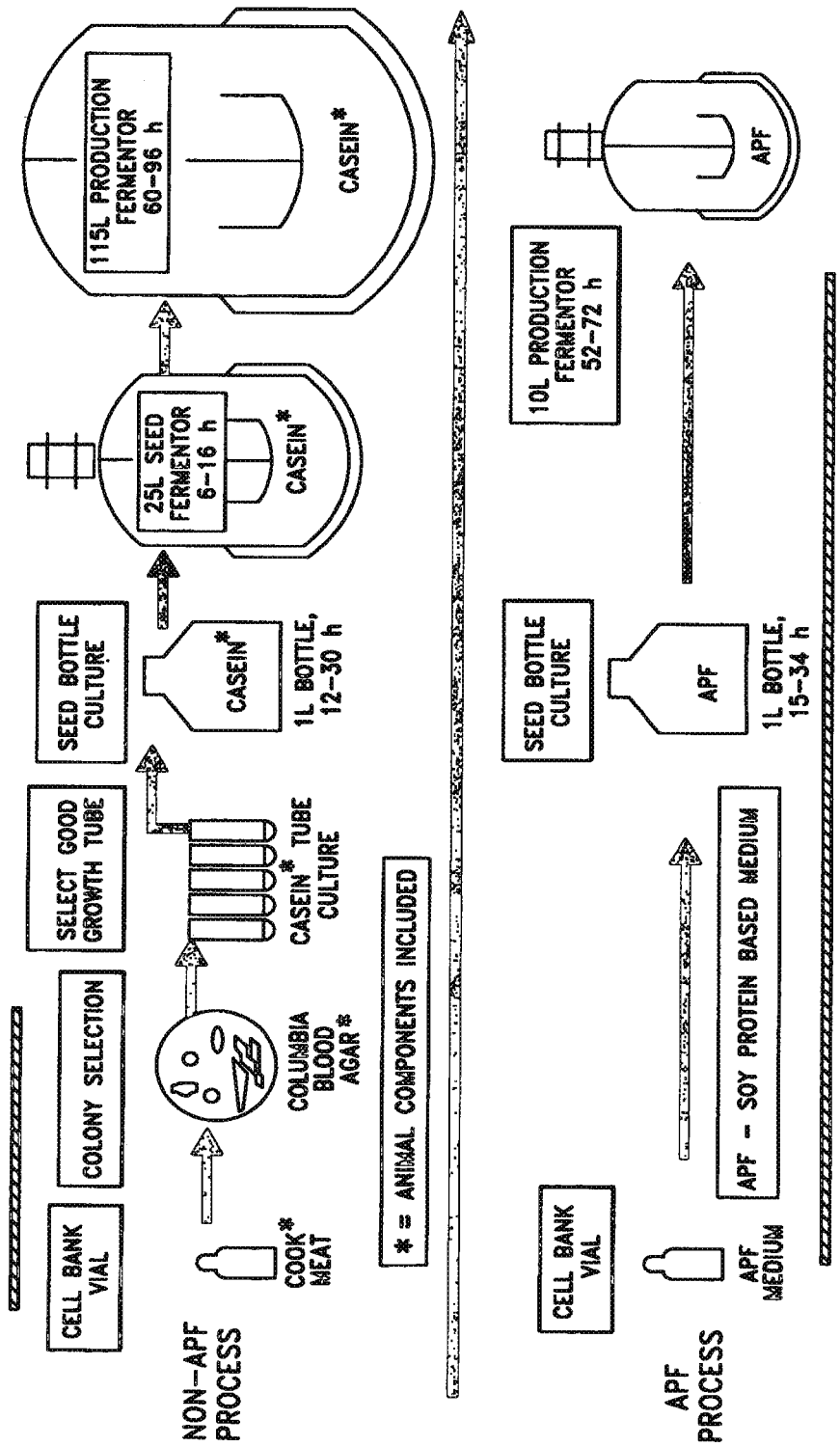

FIG. 2 presents a summary of the differences between an industrial scale (non-APF) Schantz process (Example 6 and the industrial scale APF process of Example 7, through the cell bank creation, culture and fermentation steps. FIG. 2 omits the harvest and purification steps.

The APF media can be used to select for *Clostridium botulinum* bacteria. Thus, concurrent practice of the Examples 6 and 7 initial culture steps permits isolation and growth of a *Clostridium botulinum* culture with characteristics conducive to growth and production of botulinum toxins in or on an APF medium. The transfer of *Clostridium botulinum* bacteria from a non-APF medium to an APF medium enriches for and selects for bacteria that can either adapt to the new environment or through selective die off of bacteria that cannot grow and produce in the new environment.

Example 8

Chromatographic Systems and Methods for Purifying a Botulinum Toxin

The chemicals used in the experiments set forth in Examples 8 and following included:
10N NaOH (Mallinckrodt, VWR Cat # MKH38505)
Acetic Acid, USP/FCC Grade, 99.5-100.5% (J. T. Baker, Cat # JT9522-2)
Ammonium Sulfate, Ultrapure, 99% (ICN, Cat # IC808211)
Citric Acid, USP/FCC Grade, 99.5-100.5% (J. T. Baker, Cat # JT0119-1)
Ethanol, anhydrous, denatured (JT Baker, Cat #9299-1)
Hydrochloric acid, NF/FCC Grade, 36.5-38%-Mallinckrodt-MK2612-14
Phosphoric acid, NF/FCC, 85%-88% (Mallinckrodt, Cat # MK278814)
Sodium acetate trihydrate, 99%-101%, USP/FCC (Mallinckrodt, Cat # M K735602)
Sodium chloride, USP/FCC Grade, 99.0-101.0 (Mallinckrodt, Cat # MK753204)
Sodium citrate, USP/FCC Grade, 99.0-100.5% (J. T. Baker, Cat # JT3650-1)
Sodium hydroxide, NF/FCC Grade, 95.0-100.5%-Mallinckrodt-MK768004
Sodium phosphate, dibasic Heptahydrate, USP (Mallinckrodt, Cat # MK789604)
Sodium phosphate, monobasic monohydrate, USP/FCC (Mallinckrodt, Cat # MK786812)

The chromatography resins use in the experiments below included:
Bakerbond ABx Prepscale (JT Baker, Cat #7269-02)
Butyl Sepharose FF (Amersham Biosciences, Cat #17-0980-02)
Ceramic Hydroxyapatite, Type I (Bio-Rad, Cat #158-4000)
Ceramic Hydroxyapatite, Type II (Bio-Rad, Cat #157-4200)
HiTrap HIC Selection Kit (Amersham Biosciences, Cat #17-1349-01)
HiTrap IEX Selection Kit (Amersham Biosciences, Cat #17-6002-33)

MEP Hypercel (Ciphergen, sample)
SP Sepharose HP (Amersham Biosciences, Cat #17-1087-03)

The equipment and accessories used is the experiments below included:
AKTA Purifier and AKTA FPLC Chromatography System (Amersham Biosciences)
Bottle-top 0.22 μm vacuum sterile filter (Nalgene)
Labscale TFF system and Pellicon XL50 with Biomax 100 membrane (Millipore) (this is the ultrafiltration equipment).
Masterflex L/S pump Model #77201-62 (Cole-Parmer)
Pellicon 2 Mini Holder (Millipore)
XK and HR columns (Amersham Biosciences)

The buffers used in our experiments are listed in Table 2.

TABLE 2

Buffers used in the APF purification process

| Purification Steps | Buffers used |
|---|---|
| Butyl Sepharose FF Chromatography | 1. 50 mM NaPi, 4M NaCl, pH6.0<br>2. 50 mM NaPi, 2M NaCl, pH6.0<br>3. 50 mM NaPi, 1M NaCl, pH6.0<br>4. 50 mM NaPi, pH 6.0 |
| SP Sepharose HP Chromatography | 5. 20 mM Na citrate, pH 4.0<br>6. 20 mM Na citrate, 300 mM NaCl, pH4.0<br>7. 20 mM Na citrate, 400 mM NaCl, pH4.0<br>8. 20 mM Na citrate, 1M NaCl, pH4.0 |
| Post Purification Steps | Solutions used |
| Post-column processes | 9. 50 mM NaAc, pH 4.0<br>10. 3.5M ammonium sulfate |
| Miscellaneous | 11. 0.1N NaOH<br>12. 1N NaOH |

In Table 2: buffers 1 and 2 were used to wash impurities off the column; buffers 3 and 4 was used to elute bound toxin from the column; buffer 5 was used to dilute the eluent from the Butyl column; buffer 6 was used to wash impurities off the column; buffers 7 and 8 were used to elute bound toxin from the column; buffer 8 was the UF/DF dialysis buffer; solution 9 was used to precipitate toxin, and solutions 10 and 11 were used to inactivate (clean) any toxin remaining in the columns after use.

Example 9

Selection of Preferred Chromatography Columns for use in an APF Column

Chromatographic Botulinum Toxin Purification (Capture Step) Process

This experiment established preferred chromatography columns and techniques for initial purification of a botulinum toxin type A complex from attendant impurities in a fermentation medium.

Feed Materials

Both a filtered cell culture (clarified culture) obtained from an APF process fermentation and an extract thereof prepared by hydrochloric acid precipitation were assessed as chromatography column feed materials. It was found that direct loading of the clarified culture onto a column prevented toxin precipitation and that a clarified culture feed material was much easier to handle and validate. On the other hand, use as the feed material of a clarified culture extract prepared by acid precipitation removed additional impurities and provided virus inactivation. With regard to the characteristics of process robustness, a clarified culture was determined to be the preferred feed material, as opposed to use of a hydrochloric acid precipitation preparation as the bulk botulinum toxin complex chromatography resin feed material. Hence, clarified culture was the preferred feed material.

Our studies showed that as the pH was lowered proteins (i.e. the botulinum toxin complex) started to precipitate at about pH 5, that small amounts of toxin was extracted (as most had precipitated out) at about pH 4.0, and that essentially all of the toxin had precipitation out of the solution at between pH 3.5 to 3.8. On the other hand, we found (based for example on SDS-PAGE and Western blotting) that most impurities were co-extracted with the botulinum toxin at a pH of 6.8. Hence, a preferred feed liquid pH for carrying out our purification process invention was between about pH 5-6.8, with a more preferred pH being about pH 5.5 for extraction, that is separation of the botulinum toxin from attendant impurities.

Capture Step

For the capture step botulinum toxin type A (Hall strain) cell culture filtrates were incubated with a number of chromatography resins (see below) under the manufacturer specified conditions for use of each particular column.

After washing the columns, the column bound proteins were eluted with the specified elution buffers. All eluted fractions were collected and analyzed by SDS-PAGE. The results obtained (Table 3) were confirmed by chromatography using 1 ml HiTrap or HR5/5 columns.

TABLE 3

Summary of Capture Step Results

| Separation Technique | Resin | Toxin in Flowthru | Toxin in Eluate | Separation Observed |
|---|---|---|---|---|
| Hydrophobic Interaction | Phenyl FF (HS) | − | + | + |
|  | Octyl FF | − | + | + |
|  | Butyl FF | − | + | + |
| Ion Exchange | Q FF | + | − | + |
|  | SP FF | + | − | − |
| Mixed Mode | HA Type I | + | − | − |
|  | HA Type II | + | − | − |
|  | Abx | + | − | − |
| Hydrophobic Charge-Induction | MEP | − | + | − |
| Immobilized Metal-ion Affinity | Chelating FF | + | − | − |

This experiment clearly showed that the desired separation of the botulinum toxin from other substances present was best achieved by use of hydrophobic type column chromatography. Thus, we found that the botulinum toxin bound to hydrophobic columns, but that it did not bind to an ion exchange column, such as the Q Sepharose FF column.

Among the hydrophobic columns evaluated, the weakly hydrophobic Butyl Sepharose FF gave the best resolution. Therefore, either Butyl Sepharose FF in binding mode or Q Sepharose FF in flowthru mode provided a preferred botulinum toxin capturing step.

Thus, we determined that an efficient capturing step can be carried out using a hydrophobic column, such as the Butyl Sepharose column chromatography. Presumably, the toxin binds to the Butyl column via a hydrophobic interaction. Prior to this experiment it was unknown that a botulinum toxin complex could be purified toxin directly from clarified culture using a hydrophobic chromatography column. We found that the Butyl Sepharose Fast Flow column has high binding capacity, allows fast flow rate with low back pressure and is therefore suitable for the capturing step that requires fast removal of impurities.

Example 10

Four Column APF Chromatographic System and Process for Purifying a Botulinum Toxin Complex Intermediate and Polishing Purification Steps Additional (intermediate and polishing) toxin purification steps were carried out using the toxin-containing fractions obtained from the preferred Q and Butyl columns of Example 9.

Three types of chromatography columns were found effective for such further purification of the botulinum toxin complex. A Hydroxyapatite (HA) type I column was a preferred column we used because it showed separation, but some toxin was found in the flowthru. Gel filtration with a Superdex 200 column was a more preferred column to use because it permitted purification of the 900 kDa botulinum toxin complex from the impurities, but a minor impurity band was still present on SDS-PAGE.

A most preferred column was a SP Sepharose HP column which we found to separate the botulinum toxin from impurities with very good resolution. The botulinum toxin was pure after SP Sepharose HP chromatography, based on analysis by SDS-PAGE.

TABLE 4

Summary of Column Chromatography Purification Steps

| Separation technique | Resin | Summary |
|---|---|---|
| Mixed mode | Hydroxyapatite type I | Toxin in flowthru mode, separated some impurities. |
| Gel filtration | Superdex 200 | Partially purified toxin, difficult to scale-up, low productivity. |
| Ion exchange | SP Sepharose HP | High resolution separation, pure toxin obtained. |

Based on the results of Examples 8 and 9, and as shown by Table 4, the following four column chromatography purification process was developed:
1. use of a Q Sepharose FF column for initial purification of a clarified culture. In this step impurities bound to the column and the toxin flowed through the column;
2. the eluent from the Q Sepharose FF column step 1 was then passed through a Butyl Sepharose FF column. The toxin bound to the column and was eluted off with a suitable buffer;
3. the eluent from the Butyl Sepharose FF was then passed through a Hydroxyapatite type I column. Impurities bound to the column and the toxin flowed through the column;
4. the eluent from the Hydroxyapatite type I was then passed through an SP Sepharose column. The toxin bound to the column and was eluted off with a suitable buffer.

This four column toxin purification process can be summarized as:

APF clarified culture=>$Q$(flowthru)=> Butyl(binding)=>$HA$(flowthru)=> $SP$(binding)=>purified toxin complex This four column bulk botulinum toxin complex process allowed direct loading of filtered culture supernatant onto the Q column (step 1). The flowthru was supplemented with ammonium sulfate to 0.8M before the second step of loading onto the Butyl column. For the third step, the butyl eluate was loaded onto the HA column directly, while the flowthru of the HA was diluted 4 times with deionized water and the pH was adjusted to 4.0 before loading onto the SP column for the fourth column step. This four column process required minimal sample handling at each step, and ensured that the toxin was exposed to mild buffering conditions throughout the four steps of this purification process.

A scale up of the four column purification process set forth above was used carried out upon 680 ml of filtered culture supernatant obtained from an APF botulinum toxin type A fermentation process. The results (see Table 5) show that this four column process resulted in highly in a high yield of highly purified botulinum toxin type A complex.

TABLE 5

Results of a Scale Up Purification using the Four Column Purification process.

| Toxin yield | ~30 mg per L culture based on UV and Hc-ELISA. |
|---|---|
| Toxin purity | >98%, monodisperse, 900 kDa complex based on SEC-HPLC and LS. Pure on SDS-PAGE, western blotting conforms to standard. |
| Toxin potency | 3-5 × $10^7$ MLD$_{50}$ units per mg based on mouse toxicity assays. |

Example 11

Additional Multi-Column APF Chromatography Processes for Purifying a Botulinum Toxin Complex Using the same procedures set forth in Examples 9 and 10 additional column combinations were evaluated. It was determined that each of the following four additional column combinations provided APF methods for obtaining highly purified botulinum toxin complex, as determined by SDS-PAGE.
1. Q (flowthru)=>Butyl=>SP
2. Butyl=>Q or HA (flowthru)=>SP
3. Butyl=>SP=>Q or HA (flowthru)
4. Butyl=>SP The purified toxins were further analyzed by SEC-HPLC with light scattering, capillary electrophoresis, residual DNA assay, Hc-ELISA, and MLD50. No significant differences were found among the toxins from the four different processes set forth above. The results are summarized in Table 6.

TABLE 6

Quality summary of toxin samples purified by different APF processes 1.4. above.

| SEC-HPLC/LS | Purity >99%, purer than BCC2030, but less homogeneous than BCC2030. |
|---|---|
| Capillary eletrophoresis | Identical to one another, similar to 19P and 20P Research Grade APF Toxin, but slightly different from BCC2030. |
| Picogreen DNA assay | 2-6 ng/ml, significantly lower than BCC2030. |
| Mouse toxicity assay, Hc-ELISA | Toxin potency 3.1-4.8 × $10^7$ MLD$_{50}$ units/mg toxin (by UV), or 3.8-12 × $10^7$ MLD$_{50}$ units/mg toxin (by Hc-ELISA). |
| Silver staining SDS-PAGE | Identical to one another. |

Example 12

Two Column APF Chromatography Process for Purifying a Botulinum Toxin Complex

Based on the results obtained in Example 11a two column (Butyl=>SP) column chromatography process was selected for further development.

Optimization of the First Step: Butyl Sepharose FF Toxin Capture

Feed: Feed is to the clarified culture loaded on the column. Since ammonium sulfate can affect the buffer pH, the use of NaCl to replace ammonium sulfate in Butyl column was evaluated. We found that addition of NaCl to the feed sufficient to 2M NaCl allowed the botulinum toxin complex to bind to the butyl column. Subsequently, we determined that feed at a 4M NaCl increased the binding of botulinum toxin complex to the Butyl column, such that the yield of toxin from the Butyl column was increased by 30% to 50%, as determined by Hc-ELISA, as compared to use of feed at 2M NaCl.

The addition of NaCl to the clarified culture (the feed) caused a small pH shift. However, the acceptable feed pH was established between pH 5 and pH 6 and the final pH of the feed after NaCl addition was within pH 5 and pH 6. Hence the preferred feed to use in this first step of a two column purification process has a 4M NaCl concentration and is at pH 5-6. Solid NaCl was added to the clarified culture directly to obtain the 4M NaCl concentration and this feed was then added to the Butyl column. The bound toxin was eluted from the column using a 1M NaCl elution buffer.

It was surprising that most of impurity proteins could be washed away from the column and most of toxin bound to the column could be eluted with a 1M NaCl buffer because column purification processes typically consist of 3 or more columns, except for an affinity column process. We determined that this butyl column is unique as it has the ability to remove many of the impurity proteins. Thus, after use of this column the botulinum toxin complex purity was approximately 50%.

A wash step was then carried out to remove impurities from a column. The impurities in the column came from the clarified culture feed (containing 4M NaCl) used. The optimized washing steps were: 1) Wash #1: 5CV of 50 mM NaPi, 4M NaCl, pH 6.0, and 2) Wash #2: 12CV of 50 mM NaPi, 2M NaCl, pH 6.0. When 12CV and 5CV were compared, it was found that 5CV is not sufficient in removing the impurities. while the wash is to remove impurities after loading the clarified culture in this case.

Elution (to remove toxin bound to a column). Toxin elution with 1.2M, 1.0M and 0.8M NaCl were evaluated. It was chosen to elute toxin with 1M NaCl in 50 mM NaPi, pH 6.0, based on toxin recovery and impurity removal.

Low salt wash: After elution, the column was further washed with 50 mM NaPi, pH 6.0 to remove residual impurities bound to the column for the characterization of purification process.

Cleaning: the column was cleaned with 3CV of 0.1N NaOH to inactivate any residual toxin before the disposal of used resin.

Running flow rate: The typical flow rate was 100 cm/h. The loading flow rate was between 90 cm/h and 120 cm/h depending on the back pressure.

Loading capacity: Typical loading capacity was 12.7 ml culture per ml bed, or at production scale, 10 L culture for 785 ml resin bed (BPG 100 column at 10 cm bed height).

Bed height: All columns were packed with standard 10 cm bed height.

Optimization of the Second Step: SP Sepharose HP Purification

Feed conditioning: The Butyl eluate was diluted 5 times with 20 mM Na citrate buffer, pH 4.0, and the feed pH was adjusted to 4.0. The five times dilution step was carried out to condition the hydrophobic interaction chromatography eluent for use in ion exchange chromatography. We found that the optimal feed pH for best toxin recovery was within the range of pH 4.0±0.2.

Wash step: After loading, the column was washed with 1) 5CV of 20 mM Na citrate, pH 4.0, followed by 2) 3-5CV of 20 mM Na citrate, 300 mM NaCl, pH 4.0 to remove impurities before the elution of bound toxin.

Elution step: The toxin was eluted with 20 mM Na citrate, 400 mM NaCl, pH 4.0.

High salt washing step: After elution, the column was further washed with 20 mM Na citrate, 1M NaCl, pH 4.0 to remove strongly bound impurities.

Column cleaning: The column was cleaned with ~3CV of 0.1N NaOH to inactivate residual toxin before the disposal of used resin.

Flow rate: The typical flow rate was 100 cm/h.

Load: The entire Butyl eluate was loaded onto the SP column.

Bed height: All columns were packed with standard 10 cm bed height.

Detailed operating procedures carried out with regard to this two column botulinum toxin complex purification process set forth in this Example 12 are set forth below.

1. Butyl Hydrophobic Interaction Column
Materials and Reagents Used
Chromatography System: AKTA purifier 100, Amersham Biosciences
Resin Type Butyl Sepharose FF, Amersham Pharmacia
Detection: UV (280 nm)
Equilibration Buffer/Wash Buffer #1: 50 mM NaPi, 4 M NaCl, pH 6.0
Wash Buffer #2: 50 mM NaPi, 2 M NaCl, pH 6.0
Elution Buffer: 50 mM NaPi, 1 M NaCl, pH 6.0
Low Salt Wash Buffer: 50 mM NaPi, pH 6.0
Cleaning Solution: 0.1 N NaOH
Titration Buffer: 500 mM NaPi, pH 7.2
Procedure
Column Packing and Conditioning
Equilibrate the column with at least 5-10 CV of Equilibration Buffer or until outlet pH is equivalent to inlet pH.
Sample Preparation
Measure the pH of the starting material.
Add solid NaCl to the clarified culture to the final NaCl concentration to 4 M. Addition of 4M NaCl is an example of how to condition the clarified culture for use of the clarified culture as a feed liquid in hydrophobic interaction chromatography. Adjust the pH to 5.0 to 6.0 if needed with Titration Buffer.
Column Loading
Load the clarified culture (containing 4M NaCl) and collect the flow through fraction for analysis.
Column Wash #1 (4 M NaCl Wash)
Wash the column proteins with 5CV of Equilibration Buffer to remove impurity. Collect the wash fraction for analysis and record the volume.
3.5. Column Wash #2 (2 M NaCl Wash)
Wash the column with 15CV of Wash Buffer #2 to remove additional impurity proteins. Collect the wash fraction for analysis and record the volume.
Elution (1 M NaCl Toxin Peak Elution)
Elute the bound toxin with 5 CV of Elution Buffer. Monitor the 280 nm absorbance of eluate, begin the collection of eluate when the 280 nm absorbance starts to increase and stop the collection of the eluate peak when the 280 nm absorbance reaches the baseline. Record the volume of toxin elution fraction.

Low Salt Wash (0 M NaCl Impurity Peak Elution)
Wash the column with 4CV of Low Salt Wash Buffer to remove residual impurity proteins. Collect the fraction for analysis and record the volume.
Column Cleaning (0.1 N NaOH)
Clean the column with 3 CV of Cleaning Buffer to inactivate the residual toxin before the disposal of used resin.
2. SP Cation Exchange (Post Butyl) Column
Materials and Reagents Used
Chromatography System: AKTA purifier 100, Amersham Biosciences
Resin Type: SP Sepharose HP, Amersham Pharmacia
Detection: UV (280 nm)
Dilution, Equilibration and Wash Buffer #1: 20 mM NaCitrate, pH 4.0
Wash Buffer #2: 20 mM NaCitrate, 300 mM NaCl, pH 4.0
Elution Buffer: 20 mM NaCitrate, 400 mM NaCl, pH 4.0
High Salt Buffer: 20 mM NaCitrate, 1 M NaCl, pH 4.0
Cleaning Solution: 0.1 N NaOH
Procedure
Column Packing and Conditioning
Equilibrate the column with 5-10 CV of Equilibration Buffer or until outlet pH is equivalent to inlet pH.
Sample Preparation
Dilute one volume of 1M NaCl Butyl eluate with 4 volume of Dilution Buffer. Measure the conductivity and pH of the load. Adjust the pH to 4.0 if needed.
Column Loading
Apply the above diluted Butyl eluate to SP column and collect the flow through fraction.
Column Wash #1 (Equilibration Buffer Wash)
Wash the SP column with 5CV of Equilibration Buffer. Continue to collect the eluate as flow through fraction.
Column Wash #2 (300 mM NaCl Wash)
Wash the SP column with 4CV of Wash Buffer #2 to remove impurity proteins. Record the volume of the wash #2 fraction.
Elution (400 mM NaCl Elution)
Elute the bound toxin with 3CV of Elution Buffer. Monitor the 280 nm absorbance of eluate, begin the collection of eluate when the 280 nm absorbance starts to increase and stop the collection of the eluate peak when the 280 nm absorbance reaches the baseline. Record the volume of toxin elution fraction.
High Salt Elution (1 M NaCl)
Elute the strongly bound impurity proteins with 3CV of High Salt Buffer. Collect the fraction for analysis and record the volume.
Column Cleaning
Clean the SP column with 3 CV of Cleaning Solution to inactivate the residual toxin before the disposal of used resin.

Example 13

Robustness of the Two Column APF Chromatography Process for Purifying a Botulinum Toxin Complex The robustness of the two column method of Example 12 was studied in a series of experiments, as set forth below.
Culture pH
The effect of culture pH on toxin purification was evaluated. A study using cultures grown at pH 5.5 and pH 6.5 as the starting material for the purification was performed, and it was found that the recovery from the pH 6.5 culture was slightly lower than that from the pH 5.5 culture, based on Hc-ELISA results.

Storage Time
Toxin was purified from a culture grown at pH 5.5 on the day of harvesting and after 4-day storage of the culture at 2-8° C. No difference was found, based on toxin recovery, Butyl and SP chromatograms, SDS-PAGE, and Hc-ELISA results.
Column Binding Capacity
The proposed load on the Butyl column was 12.7 ml culture per ml resin, or 10 L culture for BPG100 column (with 10 cm bed height). Butyl and SP columns were tested by loading 4× more culture. SDS-PAGE and Hc-ELISA results indicated little toxin in the flowthru fractions for both Butyl and SP columns. The capacity of Butyl and SP column is at least four times greater than that of the current load. The toxin in SP eluate was pure on SDS-PAGE. The recovery of Butyl column is 48% and the recovery of SP column was 74%, based on Hc-ELISA. The overall yield is 16 mg toxin per L culture, based on UV result.
Process Hold Time
After harvesting, the culture was processed through Butyl column on the same day or after overnight storage. Butyl eluate was normally stored overnight before loading onto the SP column. A preliminary study showed that the Butyl eluate was stable for up to 4 days, which gave identical chromatogram and SDS-PAGE patterns. The stability of SP eluate was evaluated by capillary electrophoresis (CE) and SEC-HPLC. The results showed no difference among samples stored for up to 2 days. The recovery of toxin after filtration was also evaluated for these samples. Toxin recovery was slightly decreased on day 2 compared to day 0, but it was not clear whether such decrease was due to storage or experimental variation.
Cell Density of Culture
Two times concentrated culture and 2× diluted culture were evaluated by Butyl column chromatography to study the effect of culture cell density on toxin purification. The chromatograms from both runs looked identical. The impurity and toxin profile from both runs were identical on SDS-PAGE. The Hc-ELISA results (Table 7) showed that the mass balance from both runs were >90%, while the recovery of 2× concentrated culture was significantly lower than that of 2× diluted culture. Twenty-nine percent toxin was lost before toxin elution for 2× concentrated culture, compared with 4% loss for 2× diluted culture.

TABLE 7

APF toxin mass balance analyzed by Hc-ELISA.

| Run | Mass balance | FT | 2M Wash | 1M Elution | 0M Elution |
| --- | --- | --- | --- | --- | --- |
| 2x concent. | 91% | 11% | 18% | 53% | 9% |
| 2x diluted | 97% | 0% | 4% | 74% | 19% |

Bioburden Studies
Bioburden was monitored at different steps of the process. Samples of Butyl load, Butyl eluate after 3 day storage, SP load, SP eluate, and SP eluate after overnight storage were evaluated. Some contaminants were noted (~<1 CFU/ml to 35 CFU/ml). The sample with the highest number of contaminants was the Butyl eluate. Contaminants may be due to the uncontrolled environment in which purification process was performed.
Effect of 4M NaCl
In order to evaluate the effect of 4M NaCl on the toxin in culture, the culture containing 4M NaCl was kept at 4° C. overnight and then Butyl and SP columns were performed. The chromatographic result, SDS-PAGE and Hc ELISA showed there was no effect of 4M NaCl on the toxin in the culture after overnight storage.

Culture Media (3:1:1 vs 5:1:1)

Two point five liters of 5:1:1 and 3:1:1 cultures were processed. The toxin recovery for each of the purifications analyzed by Hc-ELISA is summarized in Table 8. The toxin purified from both cultures was pure on SDS-PAGE, which indicates that the process developed with 3:1:1 culture can be used to purify toxin from 5:1:1 culture.

TABLE 8

Toxin recovery based on Hc-ELISA

| Step | 3:1:1 culture | 5:1:1 culture |
|------|---------------|---------------|
| Butyl | 46% | 43% |
| SP | 63% | 44% |

Working pH for SP Sepharose HP Chromatography

SP Sepharose HP chromatography was carried out at different pH values: 3.5, 4.2, and 4.5. It was found that pH 3.5 caused toxin precipitation in the column, no toxin was eluted with 400 mM NaCl and very little toxin came out with 1M NaCl. At pH 4.5, toxin did not bind to the SP column. Preliminary results obtained at pH 4.2 showed that the toxin did not bind as strongly as at pH 4.0 and was eluted as a broad peak after the wash peak at 300 mM NaCl. The results indicate that the pH at this step was critical and that the optimal pH range was narrow.

Example 14

Evaluation of Two Column APF Chromatography Process for Purifying a Botulinum Toxin Complex Various eluents from each of the two columns of the purification process of Example 12 were evaluated as set forth below.

A. Butyl Sepharose FF Chromatography

Filtered 3:1:1 culture was used as the feed for this experiment. Before loading the feed (clarified culture obtained from a Schantz fermentation of a *Clostridium botulinum* type A [Hall strain]) onto the Butyl Sepharose FF column (XK50/10, column diameter 5 cm, bed height 10 cm, column volume: 196 ml), 584.4 g of NaCl was added to 2500 ml of culture with stirring for ~30 min. Atypically, the feed pH was adjusted to 5.81 and the running flow rate was set at 92 cm/h (normal flow rate is 100 cm/h). The loading volume was 2800 ml.

After loading, the column was washed with 5CV or 1000 ml of 50 mM NaPi, 4M NaCl, pH 6.0, followed by 15CV or 3000 ml of 50 mM NaPi, 2M NaCl, pH 6.0. The bound botulinum toxin type A complex was then eluted from the column with 5CV or 1000 ml of 50 mM NaPi, 1M NaCl, pH 6.0. After the elution of the botulinum toxin complex, the strongly bound impurities were washed off the column with 4CV or 800 ml of 50 mM NaPi, pH 6.0. The column was next washed with 2CV (400 ml) of 0.1N NaOH to inactivate residual toxin before the disposal of used resin. The chromatogram of the toxin eluent is shown in FIG. 3.

Figure 3:
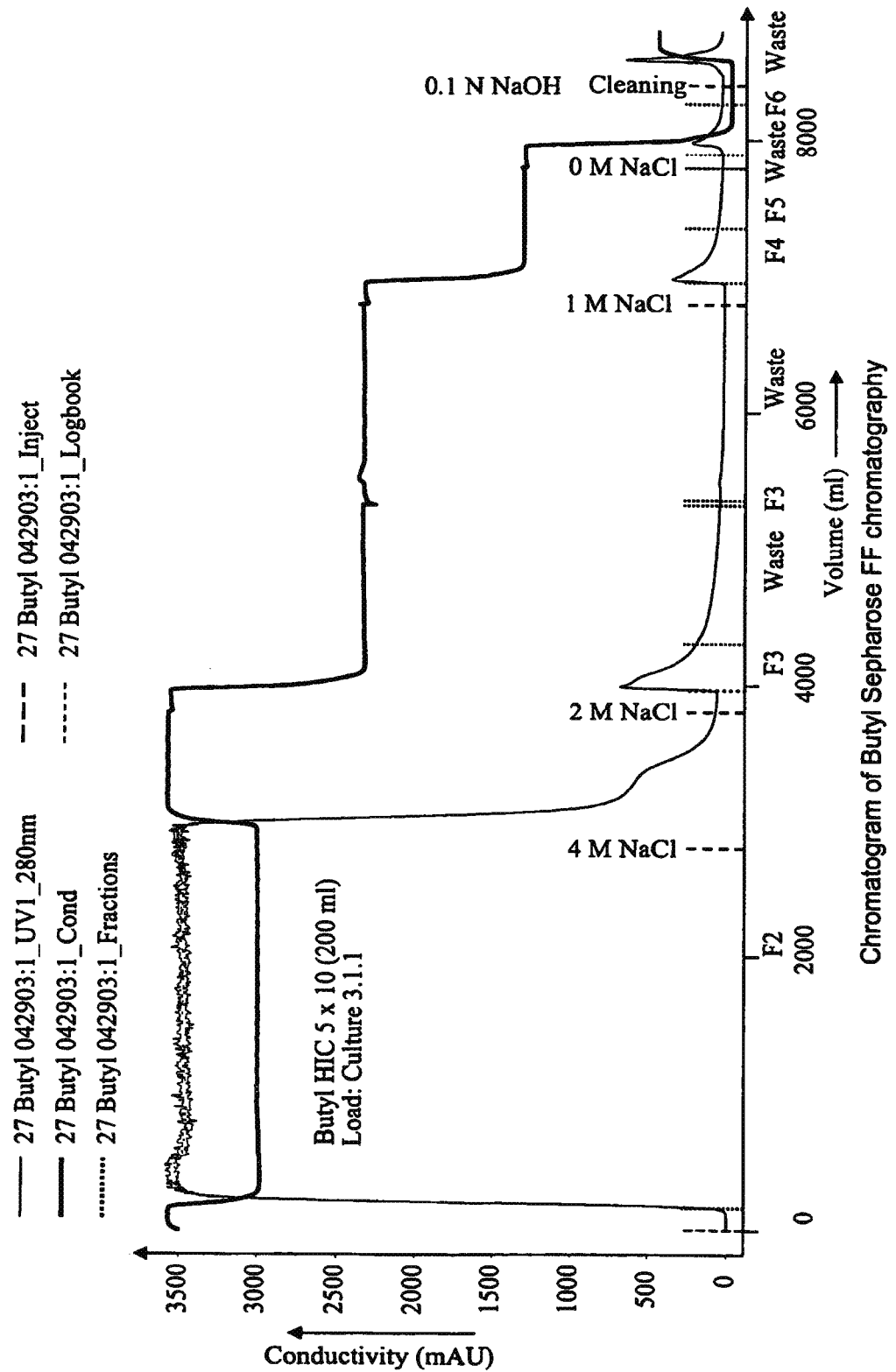

FIG. 3 shows that the Butyl column used can provide good separation of botulinum toxin complex from impurities present with it in the clarified culture feed liquid. As measured by UV280 nm, FIG. 3 shows the flow through peak and the peaks of 2M NaCl, 1M NaCl, 0M NaCl and 0.1N NaOH. Based on the peak size, it was determined that most impurities were removed in the flow through fraction. A significant amount of impurities were also removed in 2M NaCl fraction before the elution of toxin in the 1M NaCl fraction.

FIG. 3 is a chromatograph obtained from passage of an APF clarified culture (a 3.1.1 culture) through a Butyl hydrophobic interaction column. The X axis represents the volume in ml of liquid (effluent) which has passed through the column. The Y axis represents the UV absorbance at 280 nm in mAU. In addition, the conductivity (separate graph line) was monitored during chromatography.

As shown by FIG. 3, many protein impurities passed through the column in about the first approximately 3000 mls. The 4M NaCl and 2M NaCl washes buffer cause subsequent, though smaller peaks, showing removal of additional impurities. Use of the 1M NaCl (at about the 7000 ml volume) caused elution of bound toxin complex from the column and this was the fraction loaded onto the second column.

B. SP Sepharose HP Chromatography

Figure 4:
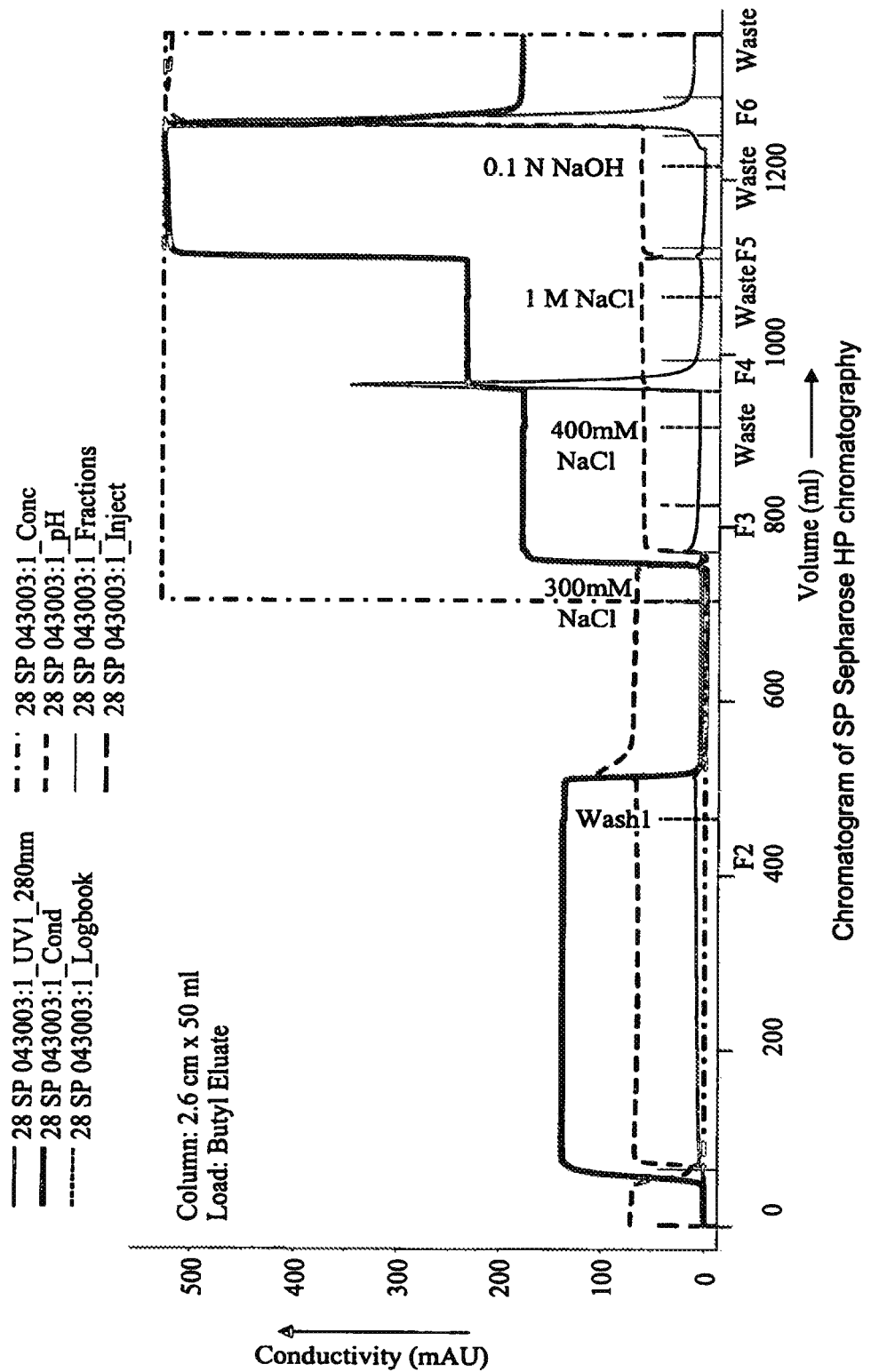

The axes in FIG. 4 are the same as they are for FIG. 3. The steps carried out to obtain the FIG. 4 chromatograph were as follows: (1) one hundred ml of the Butyl eluate obtained from Example 12 (the Butyl column eluent resulting from FIG. 3) was diluted with 400 ml of 20 mM Na citrate buffer at pH 4.0 (a five times dilution therefore). The pH of this diluted Butyl eluent was 4.1. (2) four hundred and sixty-six ml of this feed was then loaded onto the SP Sepharose HP column (XK26/10, column diameter 2.6 cm, bed height 10 cm, column volume: 53 ml).

(3) after loading the column was washed (at about the volume 450 ml point on the x axis of FIG. 4) with 5CV or 250 ml of 20 mM Na citrate, pH 4.0.

(4) the column was then washed with 4CV or 200 ml of 20 mM Na citrate, 300 mM NaCl, pH 4.0 (at about the volume 725 ml point on the x axis of FIG. 4) n.

(5) the column bound botulinum toxin complex toxin was then eluted with 3CV or 150 ml of 20 mM Na citrate, 400 mM NaCl, pH 4.0 (at about the volume 925 ml point on the x axis of FIG. 4).

(6) after elution of the column bound toxin complex, the column was further washed with 3CV or 150 ml of 20 mM Na citrate, 1M NaCl, pH 4.0 to elute strongly bound impurities (at about the volume 1050 ml point on the x axis of FIG. 4).

(7) the column was then cleaned with 3CV or 150 ml of 0.1N NaOH (just after the volume 1200 ml point on the x axis of FIG. 4).

The FIG. 4 chromatogram shows elution of a botulinum toxin type A complex (about 900 kDa molecular weight) just before the 1000 ml volume point on the x axis of FIG. 4.

FIG. 4 shows that high purified botulinum toxin complex can be obtained by use of the SP sepharose column subsequent to the Butyl column. FIG. 3 shows that there was a broad flow through peak, a small 300 mM NaCl wash peak, 400 mM toxin elution peak and 1M NaCl cleaning peak. As analyzed by SDS-PAGE in FIG. 5B, there was no visible protein band in flow through fraction, some impurity protein bands in 300 mM NaCl wash fraction and 1M NaCl cleaning fraction. Toxin was eluted in 400 mM NaCl elution fraction.

Figure 5A:
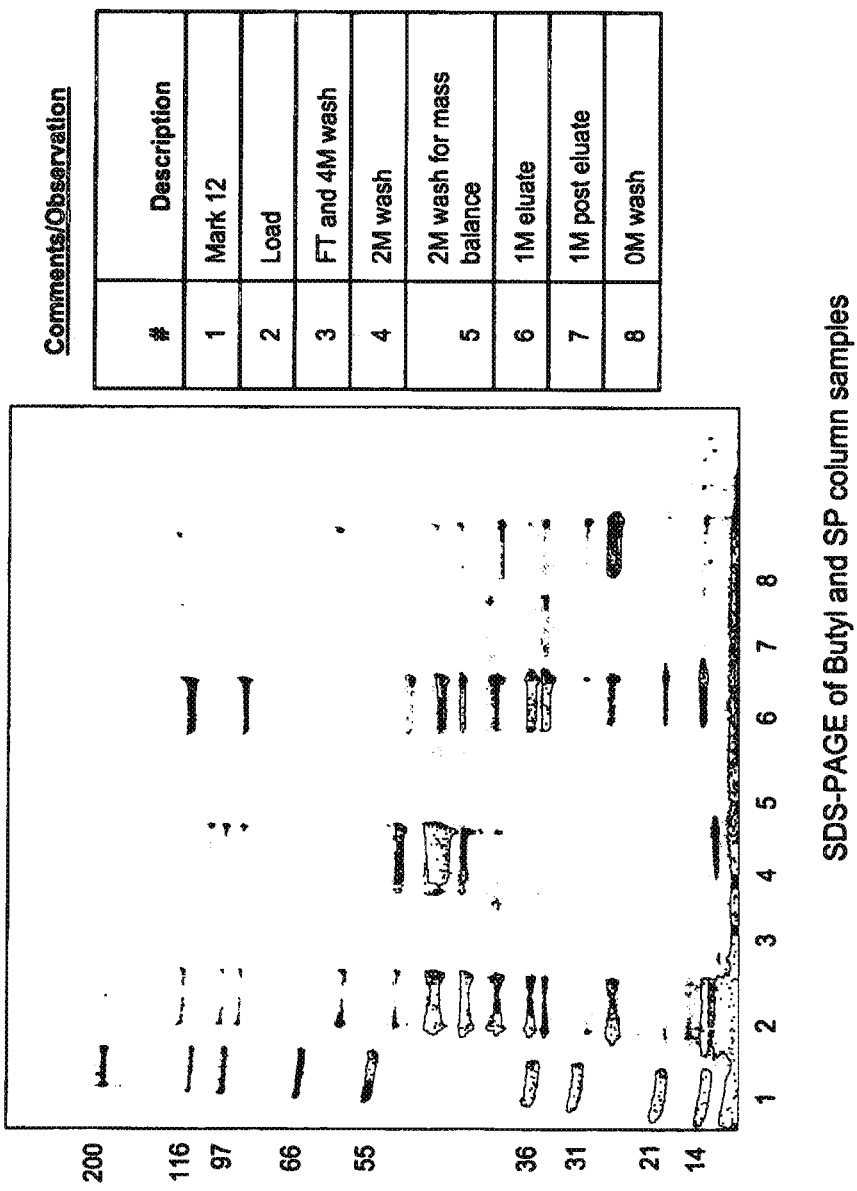
FIG. 5B is an image of reduced SDS-PAGE of various fractions obtained from operation of the SP column of FIG. 4. The left and bottom sides of FIG. 5B are marked as they are in FIG. 5A.

C. Analytical Results:

SDS-PAGE:

The elution fractions from the Butyl and SP column chromatography columns were analyzed by SDS-PAGE and the typical result is shown in FIG. 5A (Butyl column) and FIG. 4B (SP column).

Figure 5B:
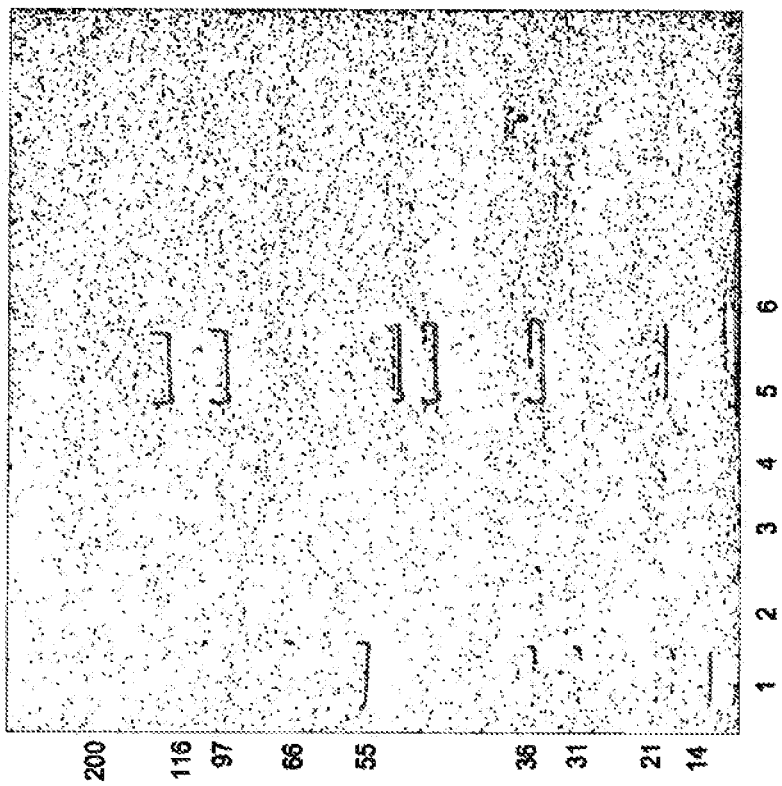
Figure 6:
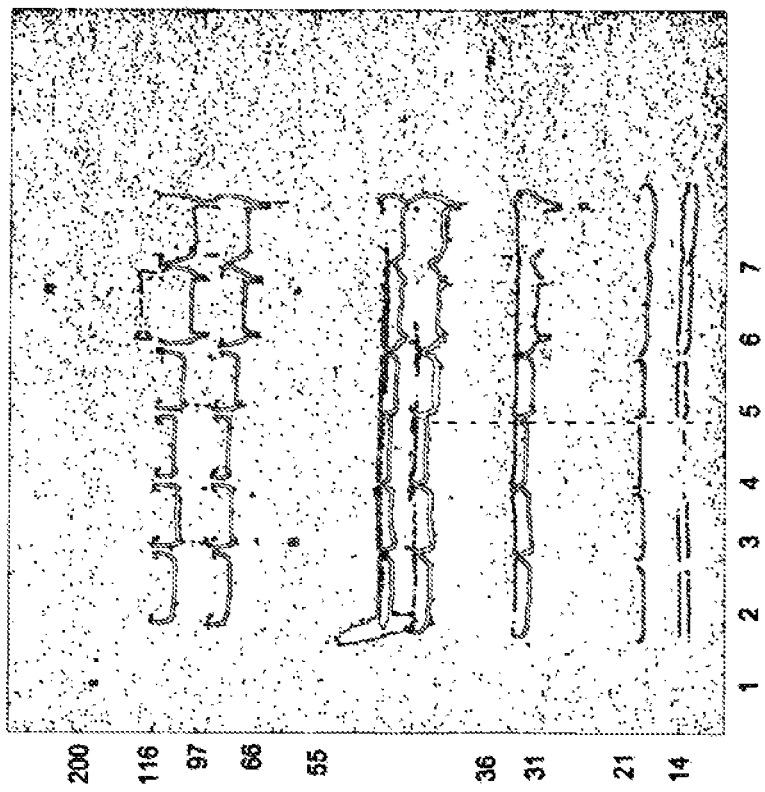
FIG. 6 is an image of reduced SDS-PAGE of various fractions obtained in post column steps (see FIG. 7), namely fractions from the UF/DF step, the sterile filtration step, and from the ammonium sulfate precipitation step. The left and bottom sides of FIG. 6 are marked as they are in FIG. 5A.

FIGS. 5 and 6 are gel electrophoresis records obtained by use of reduced SDS-PAGE. The left had side of the FIGS. 5 and 6 gel electrophoresis records is marked vertically with ascending molecular weights in thousands of Daltons (kDa).

The numbers 1 to 6, 1 to 7 or 1 to 8 is FIGS. 5 and 6 represent the fractions loaded onto the gels.

In FIG. 5A: item 1 (gel lane 1) "Mark 12" is the Novex molecular weight marker of standard molecular masses; lane 2 is the clarified culture feed liquid; lane 3 is an aliquot from the wash resulting from use of the flow through ("FT") and 4M wash in the Butyl column; lane 4 is an aliquot from use of the 2M wash; lane 5 is an aliquot from the tail fraction of the 2M wash; lane 6 is an aliquot from the fraction of 1M elution; lane 7 is an aliquot from the tail fraction of 1M elution, and; lane 8 is an aliquot from the 0M wash.

FIG. 5A shows that the Butyl column removed many impurities (see columns 3-5 in FIG. 5A) and provided initially purified botulinum toxin (see columns 6-8 in FIG. 5A).

In FIG. 5B: item 1 (gel column 1) "Mark 12" is the same molecular weight marker used in FIG. 5A; column 2 is the diluted Butyl column eluent; column 3 is an aliquot of the column flow through; column 4 is an aliquot from the 300 mM wash; column 5 is an aliquot from eluant from the column; column 6 is an aliquot from the 1M wash. FIG. 5B shows that use of an SP column subsequent to use of a Butyl column provided highly purified botulinum toxin (see column 5 in FIG. 5B).

Hc-ELISA

Toxin concentration was analyzed by Hc-ELISA, an ELISA assay to determine the toxin concentration based on the concentration of toxin heavy chain, and toxin mass balance during the purification was estimated. Table 9 shows the toxin concentration and step recovery during Butyl and SP column steps from a typical purification run. The overall recovery after Butyl and SP was 28.6%.

SEC-HPLC

The results from SEC-HPLC showed that the step recovery for SP chromatography was 42.9%, compared to 62.5% from Hc-ELISA. This shows that the recovery of botulinum toxin after the SP column step was approximately 50%.

Normalized Yield

The toxin yield was normalized as 22.3 mg (by SEC-HPLC) or 23.4 mg (by Hc-ELISA) per L culture after Butyl chromatography, and 9.6 mg (by SEC-HPLC) or 8.9 mg (by Hc-ELISA) per L culture after SP chromatography from one run. Thus, using our two column system and process set forth herein, between about 50 mg to about 90 mg of botulinum toxin complex can be purified from each 10 L of fermentation medium clarified culture (as obtained for example from the Example 6 or Example 72 fermentation processes).

TABLE 9

Toxin concentration and mass balance in typical Butyl and SP chromatography steps.

|  | Volume (ml) | Conc (µg/ml) | Toxin Amt (mg) | % Recovery |
|---|---|---|---|---|
| Butyl samples |  |  |  |  |
| Butyl Load | 2800 | 45.5 | 127.4 | 100 |
| Flowthru and Wash | 2634 | N/A | N/A | N/A |
| 2M NaCl Wash Peak | 336 | 32.5 | 10.9 | 8.6 |
| 1M NaCl Elution Peak | 404 | 144.5 | 58.4 | 45.8 |
| 1M NaCl Post Elution | 443 | N/A | N/A | N/A |
| 0M NaCl Wash | 369 | 19 | 7.0 | 5.5 |
| SP Samples |  |  |  |  |
| SP Load | 466 | 19 | 8.9 | 100.0 |
| Flowthru | 708 | N/A | N/A | N/A |
| 300 mM Wash Peak | 54 | N/A | N/A | N/A |

TABLE 9-continued

Toxin concentration and mass balance in typical Butyl and SP chromatography steps.

|  | Volume (ml) | Conc (µg/ml) | Toxin Amt (mg) | % Recovery |
|---|---|---|---|---|
| Elution Peak | 35 | 158 | 5.5 | 62.5 |
| 1M Wash Peak | 13 | N/A | N/A | N/A |
| Cleaning Peak | 44 | N/A | N/A | N/A |

Example 15

Process for Post Column Chromatography Toxin Complex Stabilization and Storage

1. Development Rationale

After column chromatography, it is preferred to transfer the purified botulinum toxin complex into a stable buffer at a desired concentration by a UF/DF step, followed by sterile filtration to thereby obtain a toxin suitable for use in a compounding of a botulinum toxin pharmaceutical composition. The purified botulinum was stored either in a soluble form in acetate buffer or as an ammonium sulfate suspension.

2. UF/DF Step

A polyethersulfone Biomax-10 membrane (NMWCO: 10 kDa, Millipore) was used in the UF/DF step. 50 mM NaAc, pH 4.0 was chosen as the diafiltration buffer. The SP eluate was ultrafiltered to ~1 mg/ml, then diafiltered with 8 diafiltration volumes (DV) of 50 mM NaAc, pH 4.0.

Ultrafiltration (UF) is a process for separating extremely small particles and dissolved molecules from fluids. The primary basis for the separation is molecular size although secondary factors such as molecule shape and charge can play a role. Materials ranging in size from 1,000 to 1,000,000 molecular weight are retained by ultrafilter membranes, while salts and water pass through. Colloidal and particulate matter can also be retained.

Diafiltration (DF) is the fractionation process that washes smaller molecules through a membrane and leaves larger molecules in the retentate without ultimately changing concentration. DF can be used to remove salts or exchange buffers. DF can also remove ethanol or other small solvents or additives. There are several ways to perform diafiltration. In continuous diafiltration, the diafiltration solution (water or buffer) is added to the sample feed reservoir at the same rate as filtrate is generated. In this way the volume in the sample reservoir remains constant, but the small molecules (e.g. salts) that can freely permeate through the membrane are washed away. Using salt removal as an example, each additional diafiltration volume (DV) reduces the salt concentration further. (A diafiltration volume is the volume of sample before the diafiltration solution is added.) Using 5 diafiltration volumes will reduce the ionic strength by ~99% with continuous diafiltration. In discontinuous diafiltration, the solution is first diluted and then concentrated back to the starting volume. This process is then repeated until the required concentration of small molecules (e.g. salts) remaining in the reservoir is reached. Each additional diafiltration volume (DV) reduces the salt concentration further. A diafiltration volume is the volume of sample before the diluting solution is added. Using 5 diafiltration volumes will reduce the ionic strength by ~96% with discontinuous diafiltration. Continuous diafiltration requires less filtrate volume to achieve the same degree of salt reduction as discontinuous diafiltration.

3. 0.22 μm Filtration Step

The low-protein-binding 0.22 μm cellulose acetate (CA) vacuum bottle-top filter was selected for the filtration step.

4. Ammonium Sulfate Precipitation Step

Ammonium sulfate precipitation was then carried out: 3.5M ammonium sulfate was added to the 0.22 μm filtered toxin solution with gentle stirring until the first appearance of opalescence. The purified bulk toxin was then stored at 2-8° C.

5. Results from a Typical Post-Column Process

SP eluate was concentrated from 70.5 ml to 18 ml using Pellicon Biomax-10 (50 cm² surface area, Millipore) on a Labscale TFF system (Millipore) and diafiltered with 8DV of 50 mM NaAc, pH 4.0. The retentate (post-UF/DF fraction) was collected and was filtered with Corning 0.22 μm CA filter (Corning 431154). The UF/DF system was rinsed with acetate buffer. The rinse fraction was collected. Ten ml of the post 0.22 μm filtrate was stored at 2-8° C. for stability studies. Eight ml of the post 0.22 μm filtrate was subjected to ammonium sulfate precipitation. A total of 2.8 ml of 3.5 M ammonium sulfate was added into the filtrate until it became opalescent.

Toxin recovery was estimated based on UV measurement, which is shown in Table 10. SDS-PAGE results are shown in FIG. 4.

In FIG. 6 the lanes shown represent:

Lane 1 is M12, molecular weight standards
Lane 2 is SP column eluate
Lane 3 is UF/DF retentate: UF/DF retentate after UF/DF of SP eluate, diluted to the same amount of loaded protein as Lane 2, for comparison
Lane 4 is UF/DF rinse solution from rinsing UF/DF membrane after completion of UF/DF membrane
Lane 5 is post 0.2 μm filtration; after UF/DF process and after the sample was filtered with the 0.22 μm filter
Lane 6 is post column ammonium sulphate suspension; after 0.22 μm filter filtration, the sample was precipitated with ammonium sulphate because the botulinum toxin complex is stable in ammonium sulphate
Lane 7 is UF/DF retentate (same as lane 3), but undiluted, to show the details FIG. 6 tells us that the post column purification process steps of UF/DF, 0.22 μm filtration, and ammonium sulphate precipitation do not affect the purity of the botulinum toxin complex, as determined by SDS-PAGE analysis. Significantly, the $MLD_{50}$ results showed that the potency of the purified bulk botulinum toxin complex was 2.9-3.7×10⁷ $MLD_{50}$ units/mg.

TABLE 10

Toxin recovery based on UV measurement

| Fraction | Toxin conc. by UV (mg/ml) | Vol. (ml) | Total toxin (mg) | Recovery (%) |
| --- | --- | --- | --- | --- |
| SP eluate | 0.389 | 70.5 | 27.4 | 100 (defined) |
| Post UF/DF | 1.260 | 18.0 | 22.7 | 82.8 |
| UF/DF rinse | 0.220 | 14.0 | 3.1 | 11.3 |
| Post filtration | 1.270 | 18.0 | 22.8 | 83.2 |
| Post AS ppt* | N/A (~0.94) | ~10.8 | N/A | N/A |

*from 8 ml post filtration fraction.

Figure 7:
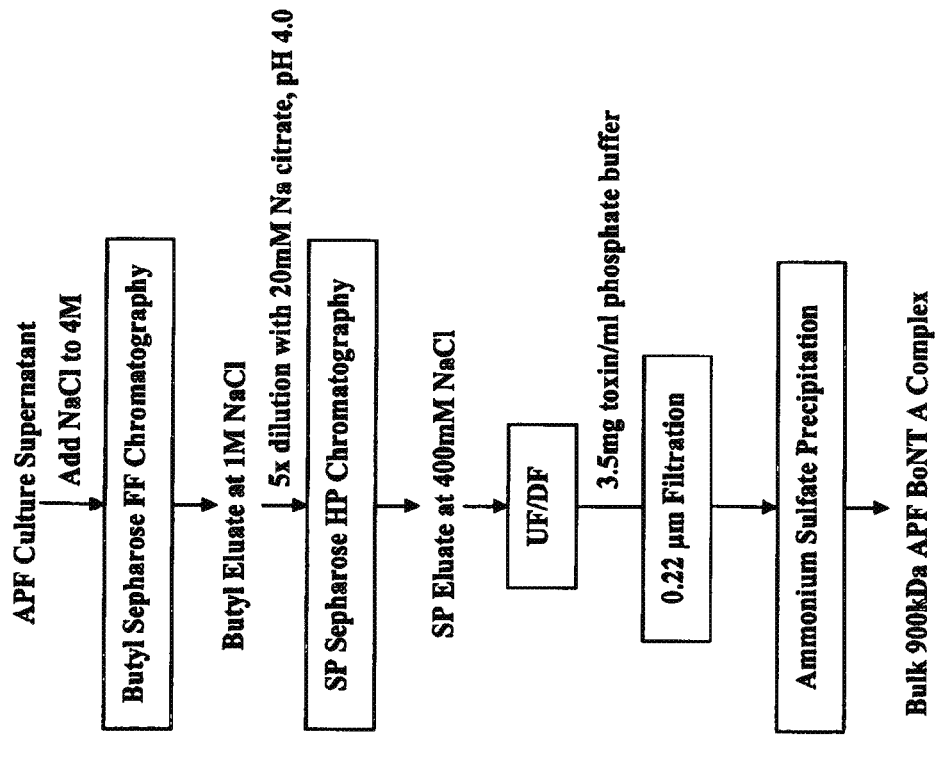
FIG. 7 is a flow chart of a APF chromatographic botulinum toxin purification process within the scope of the present invention.

FIG. 7 is a flowchart of a preferred animal protein free, two column chromatographic method for purifying a botulinum toxin type A complex. This is a robust, scalable and cGMP compliant process for obtaining purified *Clostridium botulinum* toxin 900 kDa complex. In FIG. 7 it can be noted that the Butyl eluate is conditioned for ion exchange chromatography by a five times dilution with a pH 4 sodium citrate buffer.

The FIG. 7 process can also be used to obtain pure (i.e. 150 kDa botulinum toxin free of the non-toxin complex proteins) by loading the SP column eluent onto an ion exchange column in a pH 8 buffer to disassociate the non toxin complex proteins from the 150 kDa botulinum toxin molecule, thereby providing (in the flow through from the column) a botulinum toxin type A (neurotoxic component) with an approximately 150 kD molecular weight, and a specific potency of 1-2×10⁸ $LD_{50}$ U/mg or greater. This process can also be used to obtain other non toxin components of botulinum toxin complex (i.e. non toxin hemagluttinin proteins and/or non toxin non hemaglutinin proteins) by dissociating the complex into its components and next purifying the dissociated components The purified toxin complex obtained by our process meets or exceeds the specifications set forth in Table 1. Additionally, the typical yield was approximately 100 mg of 900 kDa toxin complex from a 10 L cell culture, which is higher than the yield obtained from a Schantz (non-APF) process.

Advantages of Our Invention Include:

1. No component or substance derived from animal source is used in the process. Specifically, use of DNase and RNase are eliminated.
2. More than about 50 mg per purified botulinum toxin type A complex with the characteristics set forth in Table 1 can be obtained per 10 liters of fermentation medium.
3. The purified toxin is obtained from a process which is robust, scalable, validatable, and cGMP compliant. Robust means the process is reproducibility even upon an about ±10% change in one or more of the process parameters. Validatable means the process consistently yield purified toxin with the table 1 characteristics. cGMP means that the process can be easily converted to a manufacturing process that complies with FDA required current Good Manufacturing Practices.
4. The potency of the final purified botulinum toxin complex meets or exceeds the potency (as determined by the MLD50 assay) of purified botulinum toxin complex obtained from a Schantz or modified Schantz process.
5. elimination of any precipitation steps to purify a botulinum toxin complex.

Various publications, patents and/or references have been cited herein, the contents of which, in their entireties, are incorporated herein by reference.

Although the present invention has been described in detail with regard to certain preferred methods, other embodiments, versions, and modifications within the scope of the present invention are possible. For example, a wide variety of animal product free systems and processes (including chromatographic botulinum toxin purification processes) are within the scope of the present invention.

Accordingly, the spirit and scope of the following claims should not be limited to the descriptions of the preferred embodiments set forth above.

We claim:

1. A substantially animal protein free ("APF") process for purifying a botulinum toxin comprising the step of sequentially contacting a plurality of chromatography resins with an aqueous medium containing a botulinum toxin, wherein the plurality of chromatography resins utilized is between two to four chromatography resins, and wherein a first chromatography resin is a cation exchange resin, a second chromatography resin is a hydrophobic interaction resin, and a third chromatography resin is a mixed mode resin, thereby obtaining a purified botulinum toxin.

2. The process for purifying a botulinum toxin of claim 1, wherein the process is an essentially APF process.

3. The process for purifying a botulinum toxin of claim 1, wherein the process is an APF process.

4. The process for purifying a botulinum toxin of claim 1, wherein the aqueous medium containing the botulinum toxin results from a substantially APF fermentation process.

5. The process for purifying a botulinum toxin of claim 1, wherein the aqueous medium containing the botulinum toxin results from an essentially APF fermentation process.

6. The process for purifying a botulinum toxin of claim 1, wherein the aqueous medium containing the botulinum toxin results from an APF fermentation process.

* * * * *